(12) United States Patent
Xiong et al.

(10) Patent No.: US 11,780,963 B2
(45) Date of Patent: Oct. 10, 2023

(54) MULTI-ARM MULTI-CLAW POLYETHYLENE GLYCOL DERIVATIVE SUITABLE FOR CLICK CHEMISTRY REACTIONS

(71) Applicant: JENKEM TECHNOLOGY CO., LTD. (TIANJIN), Tianjin (CN)

(72) Inventors: Yanli Xiong, Tianjin (CN); Jinliang Wang, Tianjin (CN); Zewang Feng, Tianjin (CN); Lihui Zheng, Tianjin (CN); Xuan Zhao, Tianjin (CN)

(73) Assignee: JENKEM TECHNOLOGY CO., LTD. (TIANJIN), Tianjin (CN)

( * ) Notice: Subject to any disclaimer, the term of this patent is extended or adjusted under 35 U.S.C. 154(b) by 789 days.

(21) Appl. No.: 16/729,699

(22) Filed: Dec. 30, 2019

(65) Prior Publication Data

US 2020/0140611 A1 May 7, 2020

Related U.S. Application Data

(63) Continuation of application No. PCT/CN2018/093528, filed on Jun. 29, 2018.

(30) Foreign Application Priority Data

Jun. 30, 2017 (CN) .......................... 201710526238.1
Jun. 26, 2018 (CN) .......................... 201810670204.4

(51) Int. Cl.
*C08G 65/48* (2006.01)
*A61K 47/60* (2017.01)
*A61K 45/06* (2006.01)

(52) U.S. Cl.
CPC .............. *C08G 65/48* (2013.01); *A61K 47/60* (2017.08); *A61K 45/06* (2013.01); *C08G 2650/30* (2013.01); *C08G 2650/50* (2013.01)

(58) Field of Classification Search
CPC .................................................... C08G 65/00
See application file for complete search history.

(56) References Cited

FOREIGN PATENT DOCUMENTS

| CN | 104448296 A | 3/2015 | |
|---|---|---|---|
| CN | 104497303 A | 4/2015 | |
| CN | 106310289 A | 1/2017 | |
| EP | 2 457 591 A2 | 5/2012 | |
| WO | 2014144883 A1 | 9/2014 | |
| WO | WO-2014144883 A1 * | 9/2014 | ........... C12Q 1/6869 |
| WO | 2016183359 A1 | 11/2016 | |
| WO | WO-2016183359 A1 * | 11/2016 | ........... A61K 31/475 |
| WO | 2017/214491 A1 | 12/2017 | |

OTHER PUBLICATIONS

The State Intellectual Property Office of People's Republic of China, First Office Action, Application No. or Publication No. 201810670204.4, dated Jul. 23, 2019.
International Search Report, International application No. PCT/CN2018/093528, Date of mailing of the International search report, dated Sep. 30, 2018.
Written Opinion of the International Searching Authority, International application No. PCT/CN2018/093528, dated Sep. 30, 2018.

* cited by examiner

*Primary Examiner* — Theodore R. Howell
*Assistant Examiner* — George W Kosturko
(74) *Attorney, Agent, or Firm* — FLENER IP & BUSINESS LAW; Zareefa B. Flener

(57) ABSTRACT

The disclosure provides a multi-arm multi-claw polyethylene glycol derivative suitable for click chemistry reactions of general formula I, wherein R is a polyethylene glycol residue having a linear-chain structure, a Y-type structure or a multi-branched structure, $R_1$, $R_2$ and $R_3$ are linking groups, P is an terminal group of non-azido non-alkynyl group, D is —$N_3$ or —C≡CH, l is selected from an integer of 1 to 20, and m is selected from an integer of 0 to 19.

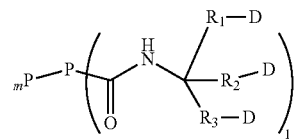

16 Claims, No Drawings

MULTI-ARM MULTI-CLAW POLYETHYLENE GLYCOL DERIVATIVE SUITABLE FOR CLICK CHEMISTRY REACTIONS

CROSS-REFERENCE TO RELATED APPLICATION

This application is a continuation application of International patent application No. PCT/CN2018/093528, filed on Jun. 29, 2018, which claims priority to Chinese patent application No. CN201710526238.1, filed on Jun. 30, 2017, and Chinese patent application No. CN201810670204.4, filed on Jun. 26, 2018. All of the aforementioned patent applications are hereby incorporated by reference in their entireties.

TECHNICAL FIELD

The disclosure relates to a polyethylene glycol derivative applicable to a click chemistry reaction, in particular to a multi-arm multi-claw polyethylene glycol derivative having a terminal azido or a terminal alkynyl, a preparation method thereof and an application thereof in click chemistry reactions.

BACKGROUND

In click chemistry, a series of reliable, efficient, selective and modular chemical reactions are utilized to generate a heteroatom-containing compound, thus realizing linking between carbon and heteroatoms. The click reaction is one of the best ways to synthesize molecules to achieve a desired function, and meanwhile avoid a complex chemical reaction. The click chemistry generally has the following characteristics that: (1) raw materials and reagents used are easily available; (2) reaction condition is simple and reaction process is not sensitive to water and oxygen; (3) yield is high, and no by-products or harmless by-products are generated; (4) stereoselectivity is good; (5) product purification is simple; and (6) product stability is good. There are mainly four types of click reactions, the most common of which is a cycloaddition reaction, especially a 1,3-dipolar cycloaddition reaction between organic azido and alkynyl or between azido and nitrile catalyzed with cuprous salt; moreover, a heterocyclic Diels-Alder reaction is also included.

Polyethylene glycol (PEG) is a polyether polymer compound with extremely wide applications, which may be applied in many fields such as pharmaceuticals, hygienics, food, chemical industry, etc. The PEG can be dissolved in water and multiple solvents, and has an excellent biocompatibility, can be dissolved in a tissue fluid in vivo, and can be rapidly discharged out of an organism without generating any toxic or side effects.

A non-patent document "Synthesis and Characterization of Azido-terminated Polyethylene Glycols" (Wang Xiaohong et al., Acta Polymerica Sinica, June 2000(3)) discloses a synthesis method of azido-terminated polyethylene glycols with a high molecular weight. However, the polymer prepared by the method is of linear-chain polyethylene glycol, which only loads one azido group on PEG molecule.

A patent document CN101787135A also discloses a synthesis method of linear structured polyethylene glycols with azido terminated, including the steps of reacting PEG with methanesulfonyl chloride, and adding sodium azide for reaction to obtain the polyethylene glycol, which can only bond one azide group on PEG molecule as well.

Patent document CN104497303A provides a multi-arm polyethylene glycol-azido derivative, and a patent document CN104448296A provides an alkynyl multi-arm polyethylene glycol derivative. The polyethylene glycol derivatives disclosed therein both have a plurality of terminal groups, thus having introduction points of a plurality of functional groups, and can load a plurality of different active terminal groups. However, the number of azido or alkynyl groups bonded in the polyethylene glycol derivatives above is still small, which cannot meet requirement of generating enough reaction sites when performing the click chemistry reaction.

In order to overcome the defects in the prior art, the disclosure provides an azido-terminated polyethylene glycol derivative or an alkynyl-terminated polyethylene glycol derivative particularly suitable for click chemistry reactions.

SUMMARY

The disclosure provides an azido-terminated or alkynyl-terminated polyethylene glycol derivative and a preparation method thereof, which solves the defects of fewer terminal azido or terminal alkynyl groups in the polyethylene glycol derivative and insufficient reaction sites during click reaction, and is particularly suitable for bonding drug molecules through a click reaction method.

According to an aspect of the disclosure, there is provided a polyethylene glycol derivative suitable for click chemistry reactions, which has a structure of general formula I:

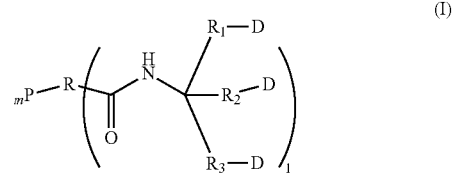

wherein:

R is a polyethylene glycol residue having a linear-chain structure, a Y-type structure or a multi-branched structure, P is an terminal group which is non-azido and non-alkynyl;

$R_1$, $R_2$ and $R_3$ are independently selected from one or a combination of more than two of —$(CH_2)_i$—, —$(CH_2)_iO(CH_2)_i$—, —$(CH_2)_iO(CH_2)_iCONH(CH_2)_i$—, —$(CH_2)_iNH$—, —$(CH_2)_iOCOO$—, —$(CH_2)_iOCONH$—, —$(CH_2)_iNHCO$—, —$(CH_2)_iNHCOO$—, —$(CH_2)_iNHCONH$—, —$OC(CH_2)_iCOO$—, —$(CH_2)_iCOO$— and —$(CH_2)_iCONH$—; and i is an integer of 0 to 10 (specifically like 0, 1, 2, 3, 4, 6, 8 or 10);

D is —$N_3$ or —$C\equiv CH$;

l is selected from an integer of 1 to 20 (specifically like 2, 3, 4, 5, 6, 7, 8, 9, 10, 12, 14, 16, 18 or 20); and m is selected from an integer of 0 to 19 (specifically like 1, 2, 3, 4, 5, 6, 7, 8, 9, 11, 13, 15, 17 or 19).

The term "having" as closed terminology does not allow for the inclusion of other components attached to the polyethylene glycol residue.

In an example of the disclosure, the P is selected from H, C1-C6 alkyl, C1-C6 alkoxy, aldehyde group, hydroxyl, amino, carboxyl, sulfydryl, ester, maleimide group, acrylic group, succinimidyl, dithiopyridyl, thioester, acryloxy, hydrazide, isocyanato, silane group, vinyl sulfone group and vitamin H residue.

In a specific example of the disclosure, the R is a linear-chain polyethylene glycol residue having a structure of formula (R-1):

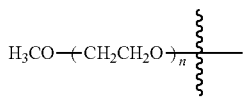
(R-1)

wherein, n is an integer of 3 to 250 (specifically like 3, 20, 50, 100, 150, 200 or 250, etc.).

In a specific example of the disclosure, the R is a Y-type polyethylene glycol residue having a structure of formula (R-2) or (R-3):

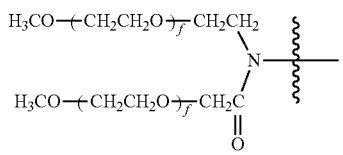
(R-2)

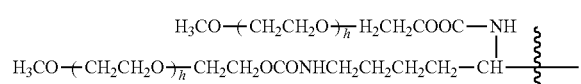
(R-3)

wherein, h and f are independently selected from an integer of 3 to 250 (specifically like 3, 20, 50, 100, 150, 200 or 250, etc.).

In a specific example of the disclosure, the R is a multi-branched polyethylene glycol residue having a structure of formula (R-4):

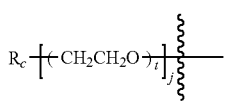
(R-4)

wherein, t is an integer of 3 to 250 (specifically like 3, 20, 50, 100, 150, 200 or 250, etc.), j is an integer of 3 to 8 (specifically like 3, 4, 5, 6, 7 or 8), $R_c$ is a core molecule of multi-branched polyethylene glycol, and is selected from residues of pentaerythritol, oligomeric pentaerythritol, methyl glucoside, sucrose, diethylene glycol, propylene glycol, glycerol and polyglycerol, and the sum of m and l is equal to j.

In an example of the disclosure, the multi-branched polyethylene glycol residue has a structure as follows:

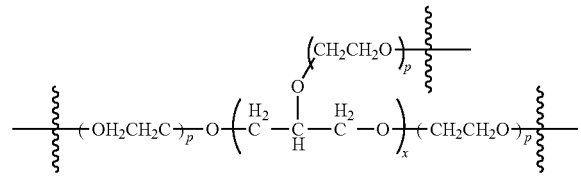

wherein, p is an integer of 3 to 250 (specifically like 3, 20, 50, 100, 150, 200 or 250, etc.);

x is selected from an integer of 1 to 18 (specifically like 1, 2, 3, 4, 5, 6, 7, 8, 9, 10, 12, 14, 16, or 18); and the sum of the m and the l is equal to x+2.

In another example of the disclosure, the multi-branched polyethylene glycol residue has a structure as follows:

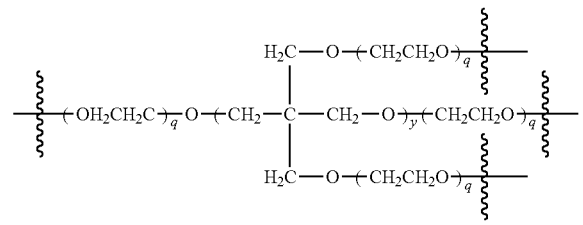

wherein, q is an integer of 3 to 250 (specifically like 3, 20, 50, 100, 150, 200 or 250, etc.), y is an integer of 1 to 9 (specifically like 1, 2, 3, 4, 5, 6, 7, 8 or 9); and the sum of the m and the l is equal to 2y+2.

In an example of the disclosure, the y is 1 or 3.

Specifically, in the polyethylene glycol derivative of the disclosure, the l is an integer selected from 3 to 8, and more specifically, the l is 4, 6 or 8.

Specifically, in the polyethylene glycol derivative of the disclosure, the m is an integer of 0 to 7, and more specifically, the m is 0.

Specifically, in the polyethylene glycol derivative of the disclosure, the x is an integer of 1 to 3, and more specifically, the x is 1, 2 or 3.

Specifically, in the polyethylene glycol derivative of the disclosure, the y is an integer of 1 to 3, and more specifically, the y is 1, 2 or 3.

Specifically, in the polyethylene glycol derivative of the disclosure, the P is selected from the following groups of $-NH_2$, $-COOH$, $-OCH_3$,

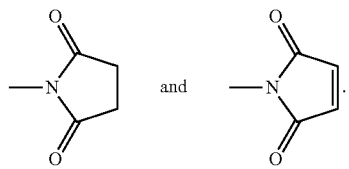

Specifically, in the polyethylene glycol derivative of the disclosure, a linking group may be further included between the terminal group P (which is non-azido and non-alkynyl) and the R, and the linking group is selected from one or a combination of more than two of $-(CH_2)_k-$, $-(CH_2)_kO(CH_2)_k-$, $-(CH_2)_kO(CH_2)_kCONH(CH_2)_k-$, $-(CH_2)_kNH-$, $-(CH_2)_kOCOO-$, $-(CH_2)_kOCONH-$, $-(CH_2)_kNHCO-$, $-(CH_2)_kNHCOO-$, $-(CH_2)_kNHCONH-$, $-OC(CH_2)_kCOO-$, $-(CH_2)_kCOO-$ and $-(CH_2)_kCONH-$; and k is an integer of 0 to 10 (specifically like 0, 1, 2, 3, 4, 6, 8 or 10).

Specifically, in the polyethylene glycol derivative of the disclosure, the i is 1, 2 or 3; and more specifically, the $R_1$, the $R_2$ and the $R_3$ are independently selected from $-(CH_2)_i-$, $-(CH_2)_iO(CH_2)_i-$ or $-(CH_2)_iO(CH_2)_iCONH(CH_2)_i-$; and is 1, 2 or 3.

In a specific example of the disclosure, the polyethylene glycol derivative has a molecular weight of 1000 Da to 80000 Da; specifically, the polyethylene glycol derivative has a molecular weight of 3000 Da to 40000 Da; and more specifically, the polyethylene glycol derivative may have a molecular weight of 3000 Da, 5000 Da, 10000 Da, 20000 Da or 40000 Da.

In an example of the disclosure, the polyethylene glycol derivative of the disclosure has a structure of general formula II:

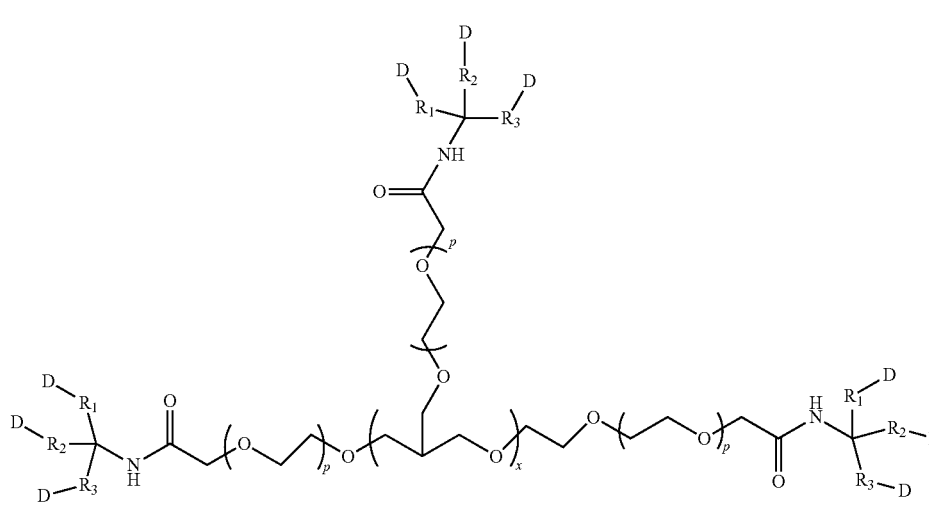

(II)

In an example of the disclosure, the polyethylene glycol derivative of the disclosure has a structure of general formula III:

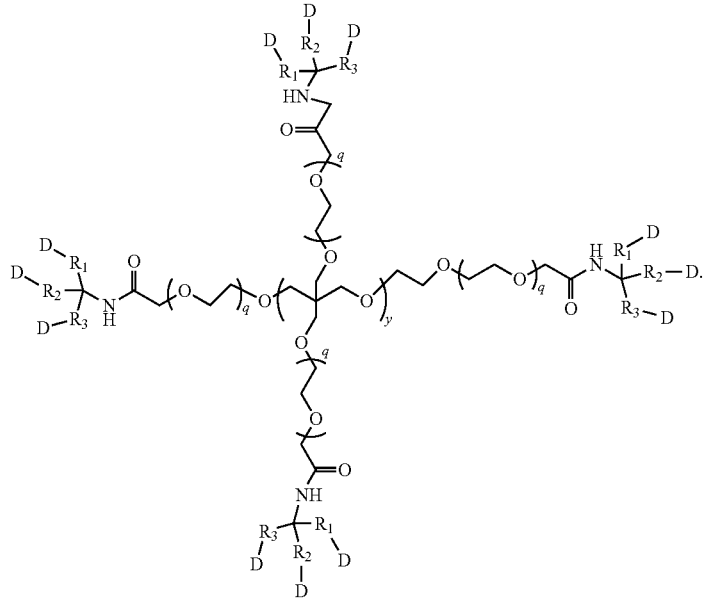

(III)

In an example of the disclosure, when the D is $-N_3$, the $R_1$, the $R_2$ and the $R_3$ are and i is an integer of 1 to 10; and specifically, the i is 1, 2 or 3.

In an example of the disclosure, when the D is CC the $R_1$, the $R_2$ and the $R_3$ are $-(CH_2)_i(CH_2)_i-$ or $-(CH_2)_iO(CH_2)_i CONH(CH_2)_i-$, and i is an integer of 1 to 10; and specifically, the i is 1, 2 or 3.

According to another aspect of the disclosure, there is provided a preparation method of the above polyethylene glycol derivative of the disclosure, which includes: (1) reacting polyethylene glycol having a linear-chain structure, a Y-type structure or a multi-branched structure or a derivative thereof with ethyl chloroformate to obtain polyethylene glycol ethyl carboxylate; (2) reacting the polyethylene glycol ethyl carboxylate with tris(hydroxymethyl)aminomethane to obtain N-[2-hydroxy-1,1-bis(hydroxymethyl)ethyl]-polyethylene glycol carboxylic acid amide; (3) reacting the N-[2-hydroxy-1,1-(hydroxymethyl)ethyl]-polyethylene glycol carboxylic acid amide with methanesulfonyl chloride to obtain N-[2-methanesulfonyloxy-1,1-bis(methanesulfonyloxymethyl)ethyl]-polyethylene glycol carboxylic acid amide; and (4) reacting the N-[2-methanesulfonyloxy-1,1-bis(methanesulfonyloxymethyl)ethyl]-polyethylene glycol carboxylic acid amide with sodium azide to obtain an azido-terminated polyethylene glycol derivative.

According to another aspect of the disclosure, there is further provided a preparation method of the above polyethylene glycol derivative of the disclosure, which includes: (1) reacting polyethylene glycol having a linear-chain structure, a Y-type structure or a multi-branched structure or a derivative thereof with ethyl chloroformate to obtain polyethylene glycol ethyl carboxylate; (2) reacting the polyethylene glycol ethyl carboxylate with tris(hydroxymethyl)aminomethane to obtain N-[2-hydroxy-1,1-bis(hydroxymethyl)ethyl]-polyethylene glycol carboxylic acid amide; and (3') reacting the N-[2-hydroxy-1,1-bis(hydroxymethyl)ethyl]-polyethylene glycol carboxylic acid amide with bromoalkyne to obtain an alkynyl-terminated polyethylene glycol derivative.

According to another aspect of the disclosure, there is further provided a preparation method of the above polyethylene glycol derivative of the disclosure, which includes: (1) reacting polyethylene glycol having a linear-chain structure, a Y-type structure or a multi-branched structure or a derivative thereof with ethyl chloroformate to obtain polyethylene glycol ethyl carboxylate; (2) reacting the polyethylene glycol ethyl carboxylate with tris(hydroxymethyl)aminomethane to obtain N-[2-hydroxy-1,1-bis(hydroxymethyl)ethyl]-polyethylene glycol carboxylic acid amide; (3") reacting the N-[2-hydroxy-1,1-bis(hydroxymethyl)ethyl]-polyethylene glycol carboxylic acid amide with tert-butyl bromoalkyl carboxylic acid to obtain polyethylene glycol carboxylic acid amide butyl tri(tert-butyl oxyacetate); and (4") hydrolyzing the polyethylene glycol carboxylic acid amide butyl tri(tert-butyl oxyacetate) to obtain polyethylene glycol carboxylic acid amide butyl tri(oxyacetic acid), and then reacting the polyethylene glycol carboxylic acid amide butyl tri(oxyacetic acid) with aminoalkyne to obtain an alkynyl-terminated polyethylene glycol derivative.

Preferably, in the preparation method of the polyethylene glycol derivative of the disclosure, the step (1) includes: adding the polyethylene glycol having the linear-chain structure, the Y-type structure or the multi-branched structure or the derivative thereof and potassium carbonate to N,N-dimethylformamide, dropwise adding ethyl chloroformate under stirring, warming up to 80° C. to 100° C. (preferably 90° C.), stirring for reaction, cooling the mixture to room temperature after reaction, pouring the mixture into ice water, stirring the mixture evenly, extracting with methylene chloride, then washing, drying, filtering, concentrating and crystallizing.

Preferably, in the preparation method of the polyethylene glycol derivative of the disclosure, the step (2) includes: step comprises: adding the product of the step (1), tris(hydroxymethyl)aminomethane and potassium carbonate to dimethyl sulfoxide, warming up to 30° C. to 50° C. (preferably 40° C.), stirring for reaction, cooling the mixture to room temperature after reaction, pouring the mixture into ice water, stirring the mixture evenly, extracting with methylene chloride, then washing, drying, filtering, concentrating and crystallizing.

Preferably, in the preparation method of the polyethylene glycol derivative of the disclosure, the step (3) includes: heating and refluxing the product of the step (2) and toluene, cooling to room temperature, adding methylene chloride and triethylamine, stirring the mixture evenly, cooling with ice water, dripping methanesulfonyl chloride for reaction, adding ethanol after the reaction is completed, and then stirring, filtering, concentrating and crystallizing.

Preferably, in the preparation method of the polyethylene glycol derivative of the disclosure, the step (4) includes: heating the product of the step (3), sodium azide and N,N-dimethylformamide to 70° C. to 100° C. (preferably 90° C.), reacting for 2 hours to 8 hours (preferably 5 hours), cooling to room temperature, adding water and a sodium chloride solution, stirring for dissolution, extracting with methylene chloride, combining organic phases, drying, filtering and concentrating, and cooling a residue and precipitating with diethyl ether to obtain a product.

Preferably, in the preparation method of the polyethylene glycol derivative of the disclosure, the step (3') includes: dissolving the product of the step (2) in tetrahydrofuran, and adding sodium hydride to react at room temperature for half an hour, adding bromoalkyne and potassium iodide, heating for 1 hour to 4 hours, preferably heating for 1 hour, cooling and adding water, concentrating and removing tetrahydrofuran, and extracting a residue with methylene chloride to obtain a final product. More preferably, the bromoalkyne is selected from bromoacetylene, bromopropyne and bromobutyne.

Preferably, in the preparation method of the polyethylene glycol derivative of the disclosure, the step (3") includes: dissolving the product of the step (2) in dimethylformamide (DMF) and adding sodium hydride to react at room temperature for 0.5 hour to 2 hours (preferably 0.5 hour), then adding tert-butyl bromoalkyl carboxylic acid for reaction, and adding water after reaction to obtain N-(trihydroxymethyl)-tetra-arm polyethylene glycol carboxylic acid amide-tert-butyl trialkyl carboxylate. More preferably, the tert-butyl bromoalkyl carboxylic acid is tert-butyl bromoacetate.

Preferably, the preparation method of the polyethylene glycol derivative of the disclosure, the step (4") includes: dissolving the resulting product in step (3") in methanol, adding a sodium hydroxide solution, heating and hydrolyzing preferably at a hydrolysis temperature of 40° C. to 80° C. for 2 hours to 6 hours, and more preferably at a hydrolysis temperature of 60° C. for 4 hours to obtain N-(trihydroxymethyl)-tetra-arm polyethylene glycol carboxamide-trialkyl carboxylic acid, dissolving the N-(trihydroxymethyl)-tetra-arm polyethylene glycol carboxylic acid amide-trialkyl carboxylic acid and N-hydroxysuccinimide in methylene chloride, adding N,N'-dicyclohexylcarbodiimide, reacting for 2 hours to 6 hours (preferably 4 hours), and then adding aminoalkyne to react to obtain a final product. More preferably, the aminoalkyne is selected from propargylamine and 3-butyn-1-amine.

The polyethylene glycol derivative of the disclosure may be combined with proteins, peptides and pharmaceutically active micromolecules, thereby improving a targeting ability and a curative effect of drugs, and reducing toxity. The proteins, the peptides and the pharmaceutically active micromolecules include, but are not limited to: analgesics and antiphlogistics, antacids, anthelmintics, antiarrhythmic drugs, antibacterial agents, anticoagulants, antidepressants, antidiabetic agents, antidiarrheals, antiepileptic drugs, antifungal agents, antipodagrics, antihypertensive drugs, antimalarials, antimigraine, antimuscarinic agents, antineoplastic agents and immunosuppressants, antiprotozoal drugs, antirheumatics antithyroids, antiviral agents, antiviral agents, anxiolytic agents, sedatives, hypnotics and tranquilizers, beta-receptor blockers, cardiac contractions, corticosteroids, antitussives, cytotoxic agents, decongestants, diuretics, enzymes, anti-Parkinson drugs, gastrointestinal drugs, histamine receptor antagonists, lipid regulators, local anesthetics, neuromuscular blockers, nitrates and antianginal drugs, nutrients, narcotic analgetics, oral vaccines, proteins, peptides and recombinant drugs, sexual hormoues and contraceptives, spermicides, and stimulants. The mode of combining the polyethylene glycol derivative suitable for click chemical reactions of the general formula I with the proteins, the peptides and the pharmaceutically active micromolecules according to the disclosure may be through a combination formed by terminal groups thereof and drug molecules as described in the patent CN102108119A.

The disclosure further provides an application of the above polyethylene glycol derivative in click chemistry reactions.

The disclosure further provides an application of the above polyethylene glycol derivative in modifying drug molecules.

The drug molecules include amino acids, polypeptides, proteins, saccharides, organic acids, alkaloids, flavonoids, quinones, terpenes, phenylpropanols, steroids, glycosides and other drugs.

In an example of the disclosure, the drug molecule is a local anesthetic, such as an amides of local anesthetic, and more specifically, such as lidocaine, prilocaine, bupivacaine, ropivacaine, mepivacaine or etidocaine, etc.

In an example of the disclosure, the drug molecule is bupivacaine.

In another example of the disclosure, the drug molecule is an antineoplastic drug molecule, such as a natural plant antineoplastic drug, and specifically like camptothecin and derivatives thereof, for example, camptothecin, topotecan, exatecan (DX-8951f), irinotecan (CPT-11), 9-aminocamptothecin, rubitecan (9-nitrocamptothecin), lurtotecan (GG-211), CKD-601, gimatecan (ST1481), BNP-1350 or BN-80915, etc.

In an example of the disclosure, the drug molecule is irinotecan.

The disclosure further provides a conjugate of the above polyethylene glycol derivative and a drug molecule, having a structure of general formula IV:

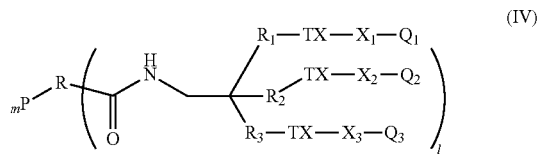

(IV)

wherein, the P, the R, the $R_1$, the $R_2$, the $R_3$, the l and the m have the above corresponding definitions of the disclosure, TX is

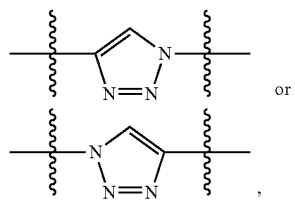

or

, $X_1$, $X_2$ and $X_3$ are linking groups independently selected from one or a combination of more than two of —$(CH_2)_a$—, —$(CH_2)_a$NH—, —$(CH_2)_a$NHCO—, —$(CH_2)_a$CONH—, —$(CH_2)_a$CO—, —$(CH_2)_a$COO—, —$(CH_2)_a$OCO—, —$(CH_2)_a$SC(O)—, —$(CH_2)_a$O—, —$(CH_2)_a$S—, $C_3$-$C_{10}$ cycloalkyl, substituted or unsubstituted aryl, and substituted or unsubstituted heterocyclyl, and a is an integer of 0 to 10, and $Q_1$, $Q_2$ and $Q_3$ are drug molecular residues, which are the same or different.

In an example of the disclosure, the $Q_1$, the $Q_2$ and the $Q_3$ are the same.

In an example of the disclosure, the drug molecule is a local anesthetic, such as an amides of local anesthetic, and more specifically, such as lidocaine, prilocaine, bupivacaine, ropivacaine, mepivacaine or etidocaine, etc.

In a specific example of the disclosure, the $Q_1$, the $Q_2$ and the $Q_3$ are the same and are all bupivacaine residues specifically with a following structure of, wherein $R_0^-$ is an anion, such as F–, Cl–, Br–, I–, mesylate, ethylsulfonate, benzene sulfonate, citrate, lactate, succinate, fumarate, glutamate, citrate, salicylate and maleate, etc.

In an example of the disclosure, the $Q_1$, the $Q_2$ and the $Q_3$ are the same and are all local anesthetic residues, and the $X_1$, the $X_2$ and the $X_3$ are independently selected from a structure as follows:

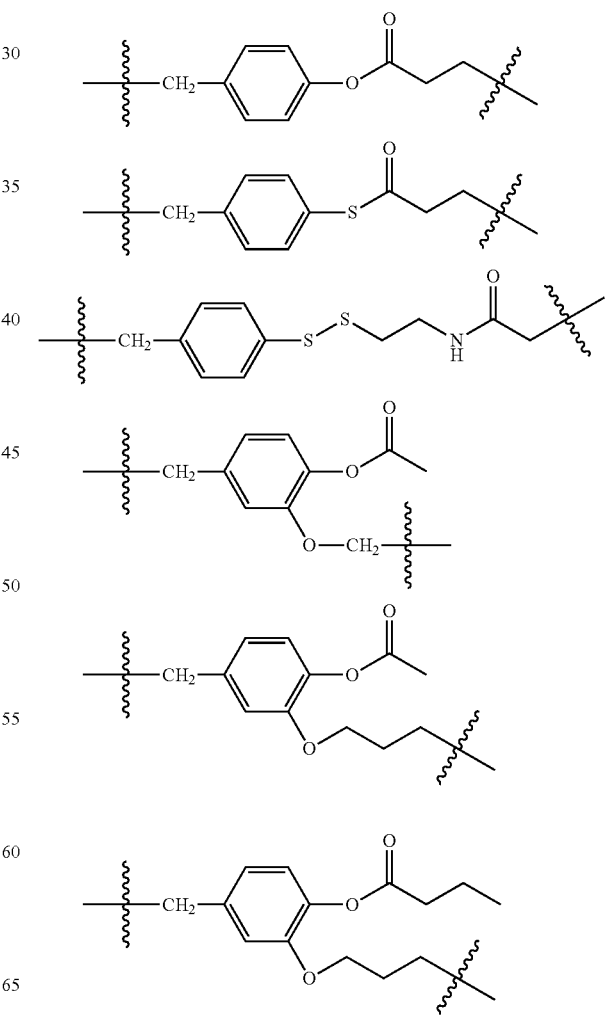

-continued

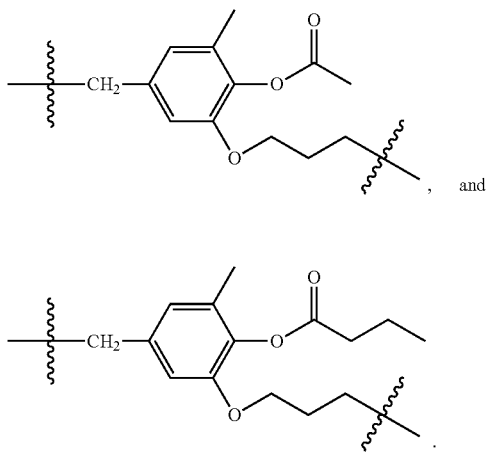
, and

In another example of the disclosure, the drug molecule is an antineoplastic drug molecule, such as a natural plant antineoplastic drug, and specifically like camptothecin and derivatives thereof, for example, camptothecin, topotecan, exatecan (DX-8951f), irinotecan (CPT-11), 9-aminocamptothecin, rubitecan (9-nitrocamptothecin), lurtotecan (GG-211), CKD-601, gimatecan (ST1481), BNP-1350 or BN-80915, etc.

In a specific example of the disclosure, the $Q_1$, the $Q_2$ and the $Q_3$ are the same and are all irinotecan residues, and specifically have a structure as follows:

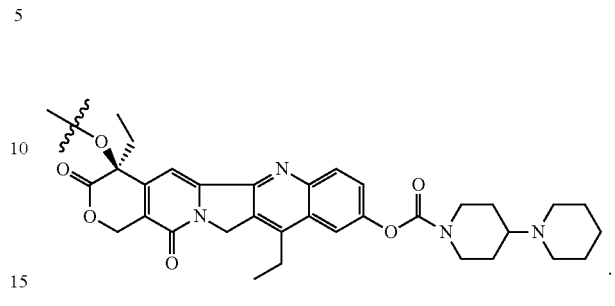

In an example of the disclosure, the $Q_1$, the $Q_2$ and the $Q_3$ are all antineoplastic drug molecule residues, the $X_1$, the $X_2$ and the $X_3$ are independently selected from —$(CH_2)_a$—, —$(CH_2)_a NH$—, —$(CH_2)_a NHCO$—, —$(CH_2)_a CONH$—, —$(CH_2)_a CO$—, —$(CH_2)_a COO$—, —$(CH_2)_a OCO$— and —$(CH_2)_a O$—, and a is an integer of 0 to 5.

In an example of the disclosure, the $X_1$, the $X_2$ and the $X_3$ are —$(CH_2)_a CO$—, such as —$CH_2 CO$—.

In an example of the disclosure, the conjugate has a structure of general formula V:

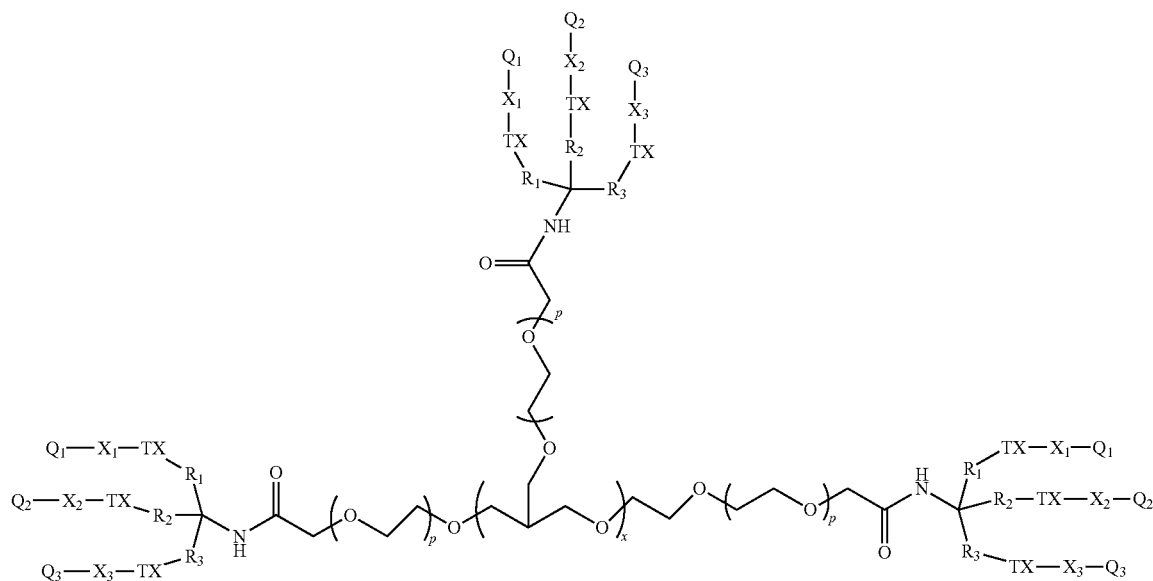

(V)

wherein, the x, the p, the TX, the $R_1$, the $R_2$, the $R_3$, the $X_1$, the $X_2$, the $X_3$, the $Q_1$, the $Q_2$ and the $Q_3$ have the above corresponding definitions of the disclosure.

In another example of the disclosure, the conjugate has a structure of general formula VI:

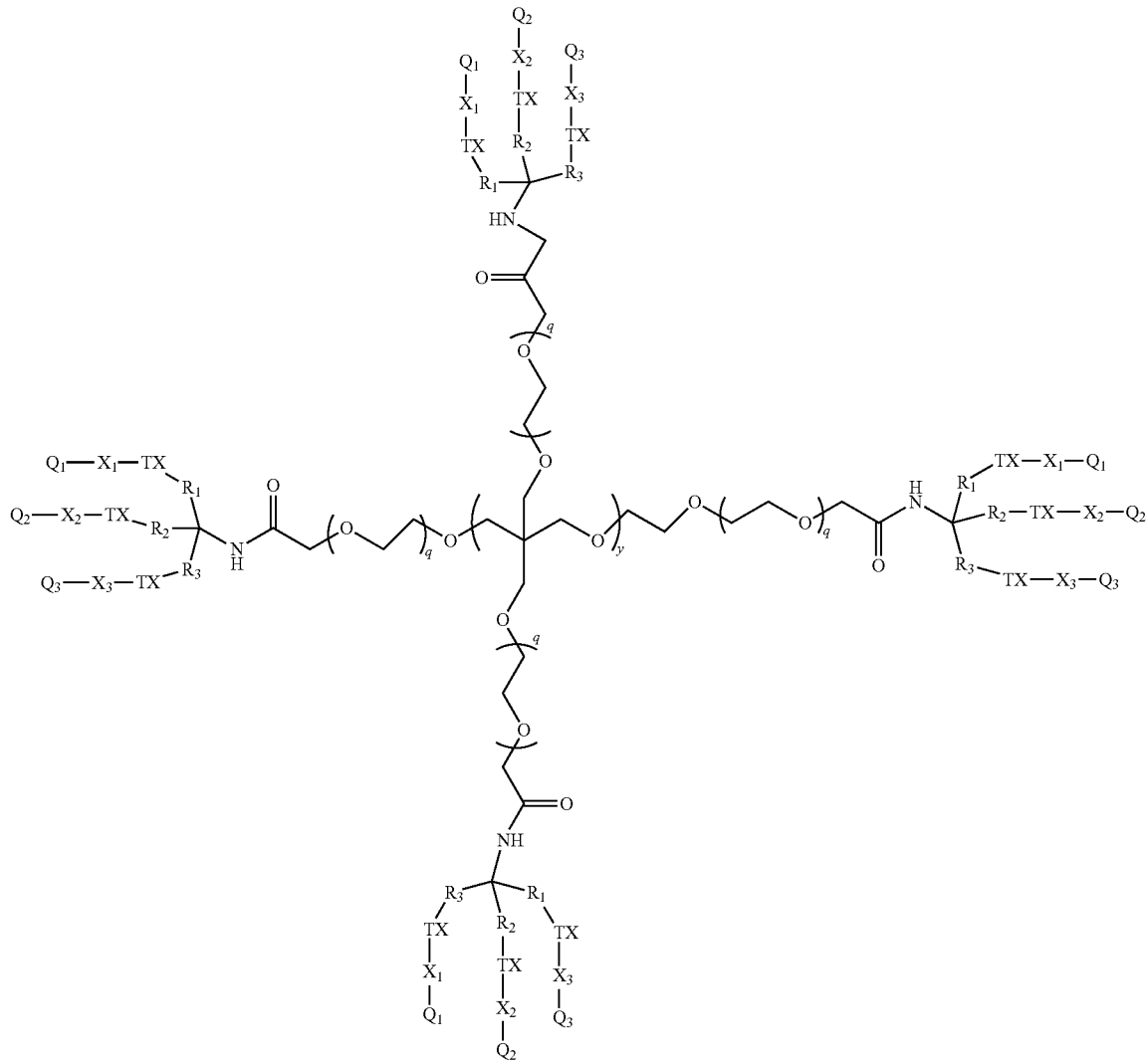

(VI)

wherein, the q, the y, the TX, the $R_1$, the $R_2$, the $R_3$, the $X_1$, the $X_2$, the $X_3$, the $Q_1$, the $Q_2$ and the $Q_3$ have the above corresponding definitions of the disclosure.

In an example of the disclosure, in the formula V, the x is 1, 2, 3, 4, 5 or 6.

In an example of the disclosure, in the formula VI, the y is 1, 2 or 3.

In an example of the disclosure, in the formulae V and VI, the $Q_1$, the $Q_2$ and the $Q_3$ are the same and are all bupivacaine residues, such as

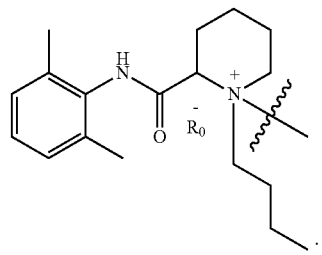

In an example of the disclosure, in the formulae V and VI, the $Q_1$, the $Q_2$ and the $Q_3$ are the same and are all irinotecan residues, such as

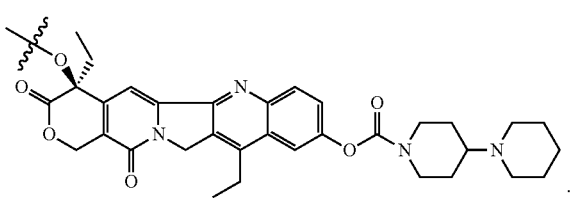 [SMILES: *O[C@]1(CC)C(=O)OCc2c1cc1n(c2=O)Cc2c-1nc1ccc(OC(=O)N3CCC(N4CCCCC4)CC3)cc1c2CC]

In an example of the disclosure, the conjugate has a structure as follows:

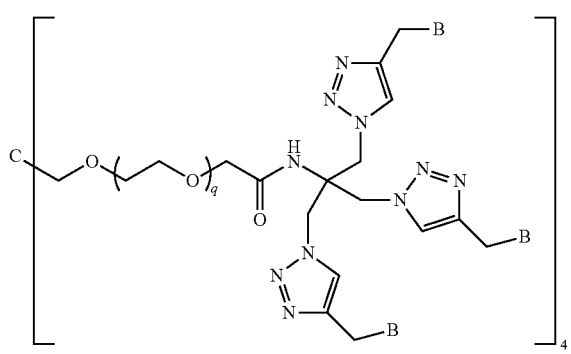

wherein, B is

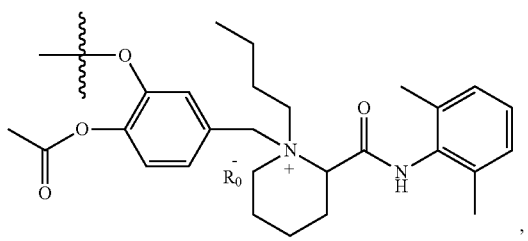

and specifically, the $R_0^-$ is $F^-$, $Cl^-$, $Br^-$ or $I^-$.

In another example of the disclosure, the conjugate has a structure as follows:

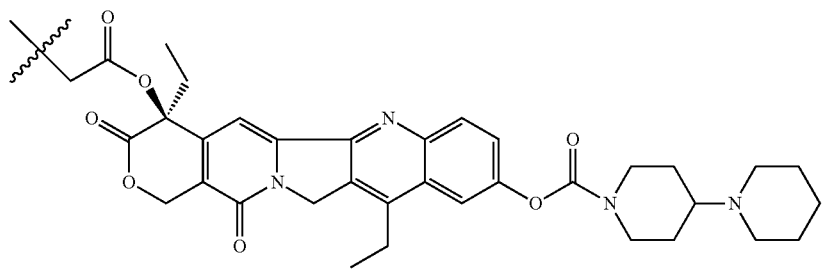

wherein, B is

The disclosure further provides a pharmaceutical composition including the conjugate of the disclosure and a pharmaceutically acceptable carrier or an excipient.

In some examples of the disclosure, the above pharmaceutical composition will include about 1 to about 99% by weight of the above composition, and 99 to 1% by weight of the suitable carrier or pharmaceutical excipient of the disclosure, depending on a desired mode of administration. Preferably, the composition includes about 5% to 75% by weight of the above composition of the disclosure, with the balance being the suitable carrier or pharmaceutical excipient. More preferably, the composition includes about 10& to 75% by weight of the above composition of the disclosure, with the balance being the suitable carrier or pharmaceutical excipient.

In some examples of the disclosure, the above pharmaceutical composition may also include a small amount of auxiliaries, such as wetting agent or emulsifier, antioxidant, etc., for example: dehydrated sorbitan monolaurate, triethanolamine oleate, butylated hydroxytoluene, etc.

In some examples of the disclosure, the above pharmaceutical composition is in the form of tablet, capsule, pill, granule, powder, suppository, injection, solution, suspension, paste, patch, lotion, drop, liniment, spray, etc.

In some examples of the disclosure, the above pharmaceutical composition may be administered by any acceptable mode of administration or used in a reagent for a similar purpose. Therefore, the mode of administration employed may be selected from oral, intranasal, parenteral, local, transdermal or rectal administration in form of solid, semi-solid or a liquid agent, such as tablet, suppository, pill, soft and hard gelatin capsules, powder, solution, suspension, injection, etc., preferably in the form of unit dose applicable to simple administration of precise dose.

A pharmaceutical composition administered in a liquid form may be employed, for example, a solution or a suspension formed by means of dissolving or dispersing the above composition of the disclosure (about 0.5 to about 20%) and an optionally present pharmaceutical adjuvant in a carrier, and an example of the carrier is selected from water, brine, glucose hydrate, glycerinum, ethyl alcohol, etc.

The disclosure further provides an application of the above conjugate of the disclosure and the pharmaceutical composition thereof in preparing a drug for preventing and/or treating a disease.

In an example of the disclosure, the disease is pain, and specifically, the pain is chronic pain, such as postoperative pain.

In an example of the disclosure, the disease is a tumor, such as colorectal cancer, lung cancer, breast cancer, pancreatic cancer, gastric cancer, esophagus cancer, colon cancer, rectal cancer, liver cancer, acute and chronic myeloid leukemia, chorionic epithelioma, bladder cancer, ovarian cancer, melanoma, etc.

The polyethylene glycol derivative of the disclosure has a plurality of azido terminal groups or alkynyl terminal groups, which not only can improve a loading rate of active terminal groups, but also can enhance a stability and safety of the azido terminal groups or the alkynyl terminal groups, and can obviously improve a drug loading capacity while being used in modifying drugs. Therefore, the polyethylene glycol derivative provided by the disclosure has a stronger flexibility and a wider application range, and has a better application prospect in aspects of organic synthesis, drug synthesis, medical device, etc.

DETAILED DESCRIPTION OF THE EMBODIMENTS

Unless otherwise defined, all the technical and scientific terms used in the disclosure have the same meaning as commonly understood by those skilled in the art to which the disclosure belongs. For example:

"Alkyl" refers to a linear-chain or branched-chain hydrocarbon chain radical without unsaturated bonds and is linked to other parts of a molecule by a single bond. A typical alkyl group contains 1 to about 12, 1 to about 8, or 1 to about 6 carbon atoms, such as methyl, ethyl, n-propyl, isopropyl, n-butyl, isobutyl, tert-butyl, n-pentyl, n-hexyl, isohexyl, or the like.

"Alkylene" refers to a linear-chain or branched-chain hydrocarbon chain radical without unsaturated bonds and the hydrocarbon chain radical is linked to other two parts of a molecule by a single bond. A typical alkylene group contains 1 to about 12, 1 to about 8, or 1 to about 6 carbon atoms, such as methylene (—CH$_2$—), ethylidene (—CH$_2$CH$_2$—), propylidene (—CH$_2$CH$_2$CH$_2$— or —CH(CH$_3$)CH$_2$—), etc.

"alkoxy" refers to a substituent formed after hydrogen in hydroxyl is substituted by alkyl, such as C1-C6 alkoxy, and specifically like methoxy, ethoxy, propoxy, butoxy, or the like.

"Aryl" refers to simple ring or multiple ring radicals, including a multiple ring radical containing monoaryl groups and/or fused aryl groups, such as containing 1 to 3 simple rings or fused rings and 6 to 18 carbocyclic atoms, specifically like C6 to C12 aryl groups, such as phenyl, naphthyl, xenyl, indenyl, or the like. In an example of the disclosure, the aryl is phenyl.

"Cycloalkyl" refers to alicyclic hydrocarbon, such as containing 1 to 4 simple ring and/or fused rings, containing 3 to 18 carbon atoms, and preferably containing 3 to 10 carbon atoms, such as cyclopropyl, cyclohexyl or adamantyl, etc.

"Heterocyclyl" includes heteroaromatic groups and heteroalicyclic groups containing 1 to 3 simple rings and/or fused rings and 3 to about 18 ring atoms, specifically like heteroaromatic groups and heteroalicyclic groups containing 5 to about 10 ring atoms. In the disclosure, suitable heteroaryl groups contain 1, 2 or 3 kinds of heteroatoms, and the heteroatoms are selected from N, O or S atoms.

The above groups may be substituted by one or more suitable groups at one or more available positions, such as: OR', =O, SR', SOR', SO$_2$R', OSO$_2$R', OSO$_3$R', NO$_2$, NHR', N(R')$_2$, =N—R', N(R')COR', N(COR')$_2$, N(R')SO$_2$R', N(R')C(=NR')N(R')R', N$_3$, CN, halogen, COR', COOR', OCOR', OCONHR', OCON(R')$_2$, CONHR', CON(R')$_2$, CON(R')OR', CON(R')SO$_2$R', PO(OR')$_2$, PO(OR')R', PO(OR')N(R')R'), C$_1$-C$_{12}$ alkyl, C$_3$-C$_{10}$ cycloalkyl, C$_2$-C$_{12}$ alkenyl, C$_2$-C$_{12}$ alkynyl, aryl, and heterocyclyl, wherein each R' group is independently selected from hydrogen, OH, NO$_2$, NH$_2$, SH, CN, halogen, COH, CO alkyl, COOH, C$_1$-C$_{12}$ alkyl, C$_3$-C$_{10}$ cycloalkyl, C$_2$-C$_{12}$ alkenyl, C$_2$-C$_{12}$ alkynyl, aryl, and heterocyclyl.

In addition, some specific groups involved in the disclosure and chemical structures thereof correspond to the followings: hydroxyl, —OH; aldehyde group, —CHO; amino, —NH$_2$; maleimide group,

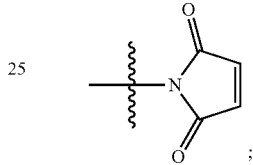

carboxyl,

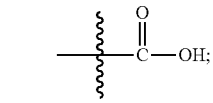

ester,

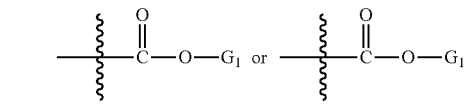

(wherein G$_1$ may be alkyl, aryl or heterocyclyl, such as methyl, ethyl, n-propyl, t-butyl, maleimide group, succinimidyl,

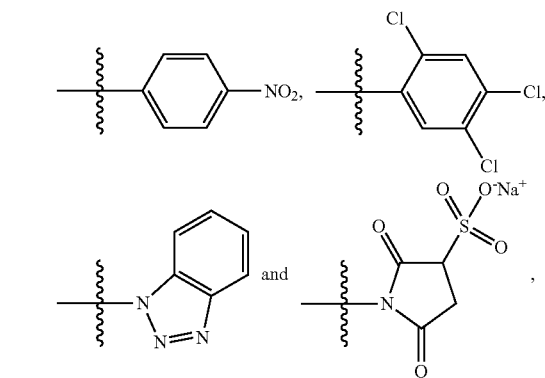

etc.); sulfydryl, —SH; acrylic group,

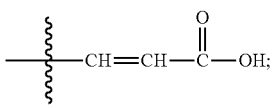

succinimidyl,

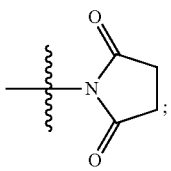 [SMILES: *N1C(=O)CCC1=O]

dithiopyridyl, such as 2-pyridyldithio

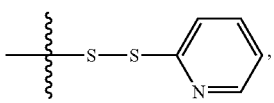

and 4-pyridyldithio,

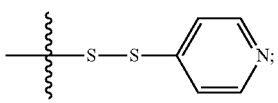 [SMILES: *SSc1ccncc1]

thioester

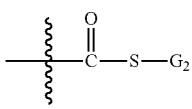

(wherein G2 may be alkyl, such as methyl, ethyl, n-propyl, tert-butyl, etc.); acryloxy,

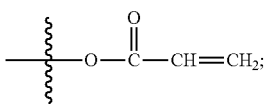

hydrazide,

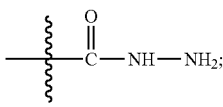 [SMILES: *C(=O)NN]

isocyanato,

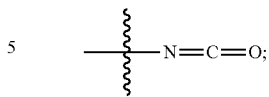

silane group, (wherein $G_3$, $G_4$ and $G_5$ may be alkylalkoxy, which are the same or different, such as methyl, ethyl, propyl, butyl, pentyl, methoxy, ethoxy, propoxy, butoxy, or the like; and preferably, the $G_3$, $G_4$ and $G_5$ are the same and are all methyl, ethyl, n-propyl, methoxy, ethoxy, n-propoxy, etc.); vinyl sulfone group,

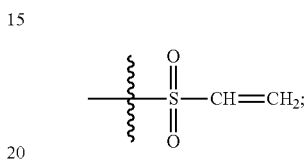

and and vitamin H residue,

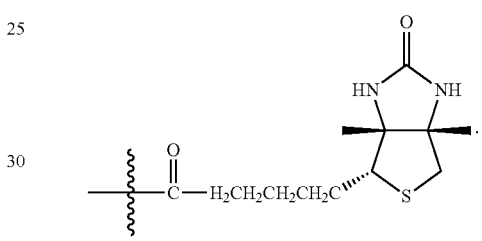

The following describes the multi-arm multi-claw polyethylene glycol of the disclosure and the derivative thereof, the conjugate with the drug molecules and the pharmaceutical composition containing the conjugate with reference to the examples, which do not limit the disclosure, and the scope of protection of the disclosure is defined by the claims. Unless otherwise stated, the polyethylene glycol used in the examples was provided by Beijing JENKEM Technology Co., Ltd., and other reagents were purchased from Beijing Chemical Reagent Co., Ltd.

Example 1 Preparation of Tetra-Arm Polyethylene Glycol (10K) Ethyl Carboxylate

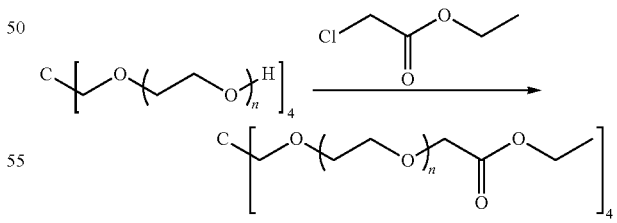

Tetra-arm polyethylene glycol (10K) and potassium carbonate were added to 40 mL of dried N,N-dimethylformamide (DMF), and added dropwise with ethyl chloroformate under stirring, after adding dropwise, a temperature was warmed up to 90° C. and then the mixture was stirred overnight; after reaction, the mixture was cooled to room temperature, poured into ice water, stirred evenly, and extracted with methylene chloride, and then the extracted solution was washed with diluted hydrochloric acid and saturated brine respectively, and dried. The remaining was filtered and concentrated, and residues were crystallized with isopropanol to obtain a white solid. $^1$H NMR: (DMSO): 1.23 (t, 12H), 3.53 (m, 900H), 3.66 (s, 8H), 4.25 (m, 8H), 4.37 (s, 8H).

Example 2 Preparation of N-[2-hydroxy-1,1-bis(hydroxymethyl)ethyl]-tetra-arm polyethylene glycol (10K) Carboxylic Acid Amide

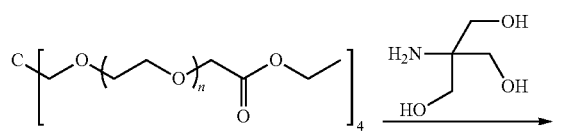

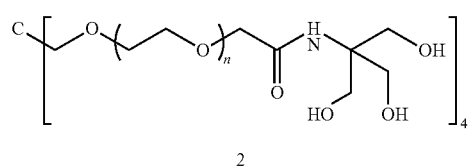

A compound 1 (prepared in Example 1), tri(hydroxymethyl)aminomethane and potassium carbonate were added to dimethyl sulfoxide (DMSO), warmed up to 40° C. and stirred overnight, after reaction, the mixture was cooled to room temperature, poured into ice water, stirred evenly, and extracted with methylene chloride, and then the extracted solution was washed with diluted hydrochloric acid and saturated brine respectively, and dried. The remaining was filtered and concentrated, and residues were crystallized with isopropanol to obtain a white solid. $^1$H NMR: (DMSO): 3.46 (s, 24H), 3.53 (m, 900H), 3.66 (s, 8H), 4.37 (s, 8H), 8.20 (s, 4H).

Example 3 Preparation of N-[2-methanesulfonyloxy-1,1-bis(methanesulfonyloxymethyl)ethyl]-tetra-arm polyethylene glycol (10K) Carboxylic Acid Amide

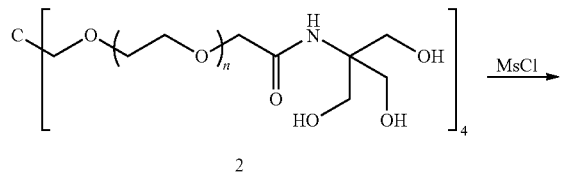

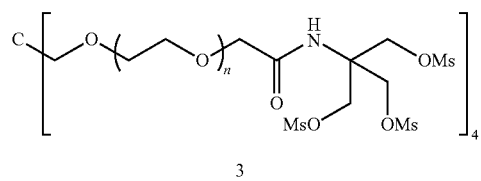

A compound 2 (60 g, 3 mmol, prepared in Example 2) and toluene (600 mL) were added to a reaction flask, heated and refluxed; after 120 mL of toluene was distilled off, the heating was stopped; after the remaining was cooled to room temperature, methylene chloride (60 mL) and triethylamine (5.4 mL) were added, stirred evenly, cooled with ice water, and then added dropwise with methanesulfonyl chloride (MsCl, 2.8 mL), and after adding dropwise, a cold bath was removed, and the remaining was naturally raised at a room temperature, and then reacted overnight. Ethanol (6 mL) was added to the reaction system next day, stirred and filtered, and then concentrated, and residues were added with isopropanol, heated for dissolved clarification, and then cooled and crystallized. The remaining was filtered and dried to obtain 59 g of product. $^1$H NMR: (DMSO): 3.16 (s, 36H), 3.53 (m, 900H), 3.66 (s, 8H), 3.81 (s, 24H), 4.37 (s, 8H), 8.20 (s, 4H).

Example 4 Preparation of N-[2-azido-1,1-bis(azidomethyl)ethyl]-tetra-arm polyethylene glycol (10K) Carboxylic Acid Amide

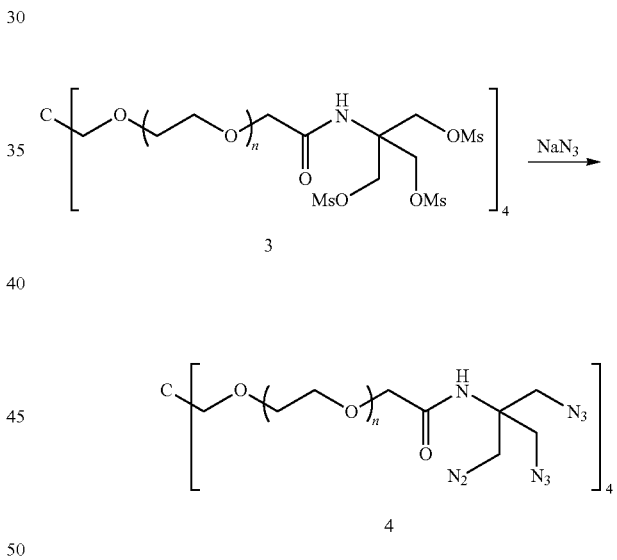

A compound 3 (58.9 g, 2.94 mmol, prepared in Example 3) and sodium azide (3.1 g, 47 mmol) were added to a reaction flask, added with N,N-dimethylformamide (295 mL), and heated to 90° C. and reacted for 5 hours, then the heating was stopped, and after the mixture was cooling to room temperature, water (295 mL) and 15% sodium chloride solution were added to a system, stirred for dissolution, extracted with methylene chloride (240 mL+180 mL+120 mL), then organic phases were combined, and the remaining was dried. The remaining was filtered and concentrated, and residues were cooled and then precipitated with diethyl ether, then subjected to suction filtration, and dried to obtain 52 g of product. $^1$H NMR: (DMSO): 3.41 (s, 24H), 3.53 (m, 900H), 3.66 (s, 8H), 4.37 (s, 8H), 8.20 (s, 4H).

Example 5 Preparation of Oct-Arm Polyethylene Glycol (20K) Ethyl Carboxylate

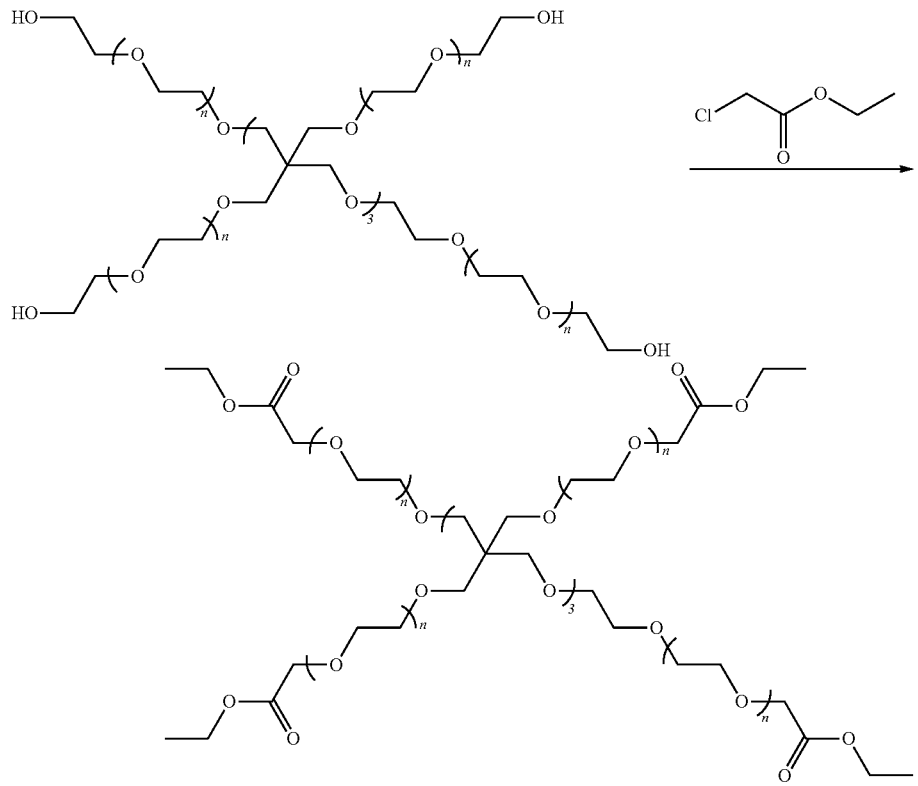

Oct-arm polyethylene glycol (20K) and potassium carbonate were added to 40 mL of dried DMF, and added dropwise with ethyl chloroformate under stirring, after adding dropwise, a temperature was warmed up to 90° C. and then the mixture was stirred overnight; after reaction, the mixture was cooled to room temperature, poured into ice water, stirred evenly, and extracted with methylene chloride, and then the extracted solution was washed with diluted hydrochloric acid and saturated brine respectively, and dried. The remaining was filtered and concentrated, and residues were crystallized with isopropanol to obtain a white solid. $^1$H NMR: (DMSO): 1.25 (t, 24H), 3.53 (m, 1800H), 3.82 (s, 16H), 4.28 (m, 16H), 4.46 (s, 16H).

Example 6 Preparation of N-[2-hydroxy-1,1-bis(hydroxymethyl)ethyl]-oct-arm polyethylene glycol (20K) Carboxylic Acid Amide

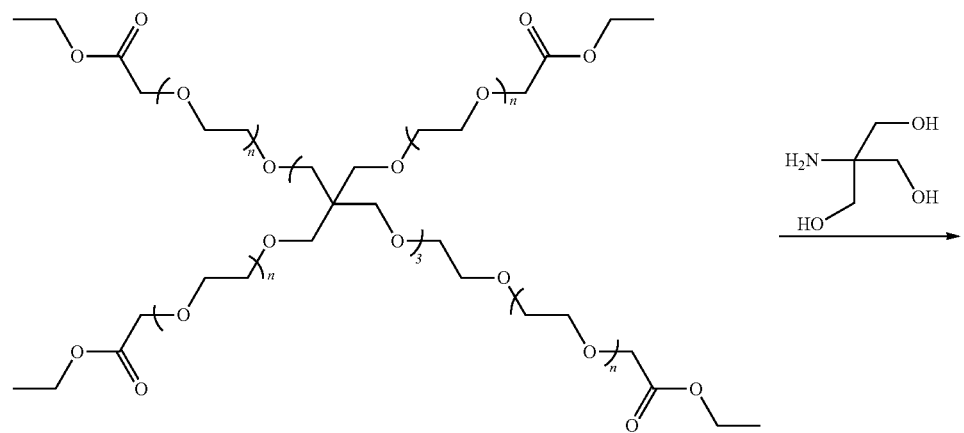

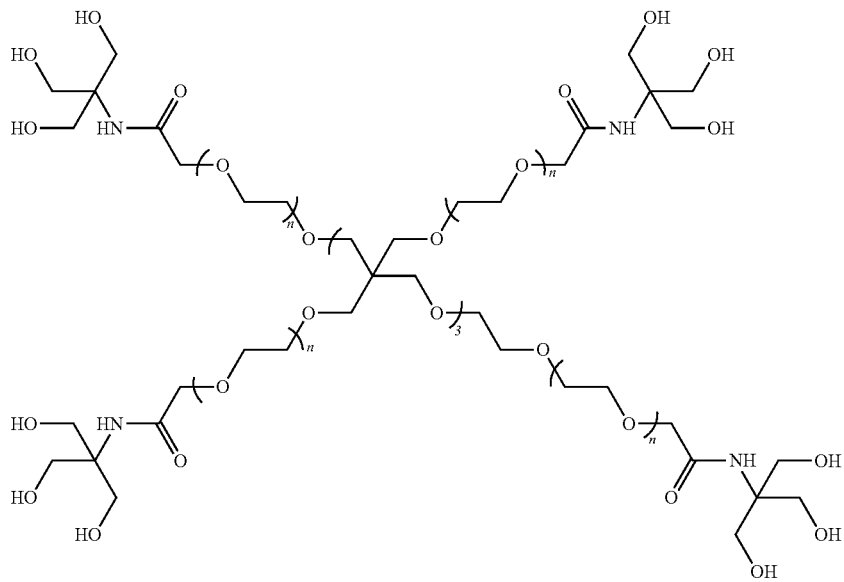

6

A compound 5 (prepared in Example 5), tri(hydroxymethyl)aminomethane and potassium carbonate were added to DMSO, warmed up to 40° C. and stirred overnight; after reaction, the mixture was cooled to room temperature, poured into ice water, stirred evenly, and extracted with methylene chloride, and then the extracted solution was washed with diluted hydrochloric acid and saturated brine respectively, and dried. The remaining was filtered and concentrated, and residues were crystallized with isopropanol to obtain a white solid. $^1$H NMR: (DMSO): 3.53 (m, 1800H), 3.63 (s, 48H), 3.82 (s, 16H), 4.28 (m, 16H), 8.20 (s, 8H).

Example 7 Preparation of N-[2-methanesulfonyloxy-1,1-bis(methanesulfonyloxymethyl)ethyl]-oct-arm polyethylene glycol (20K) Carboxylic Acid Amide

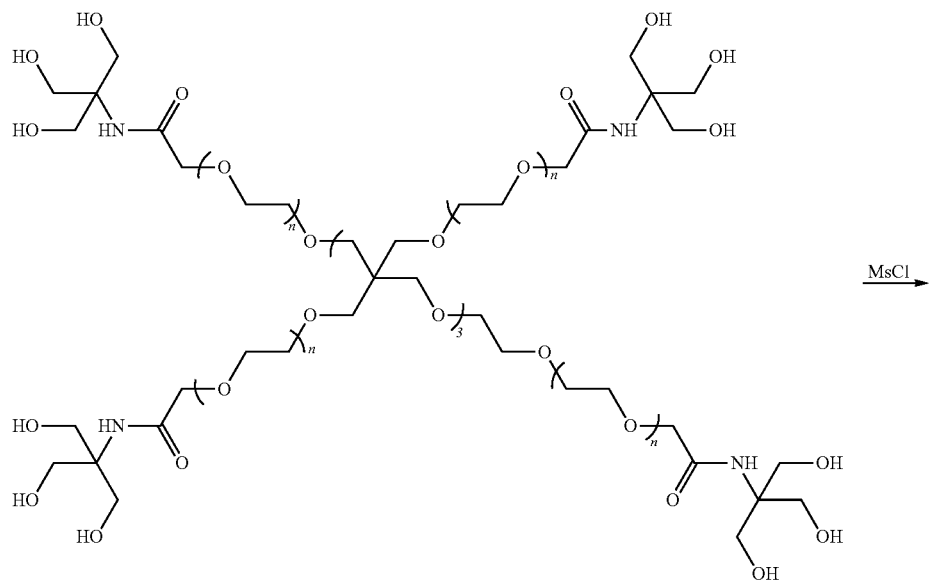

6

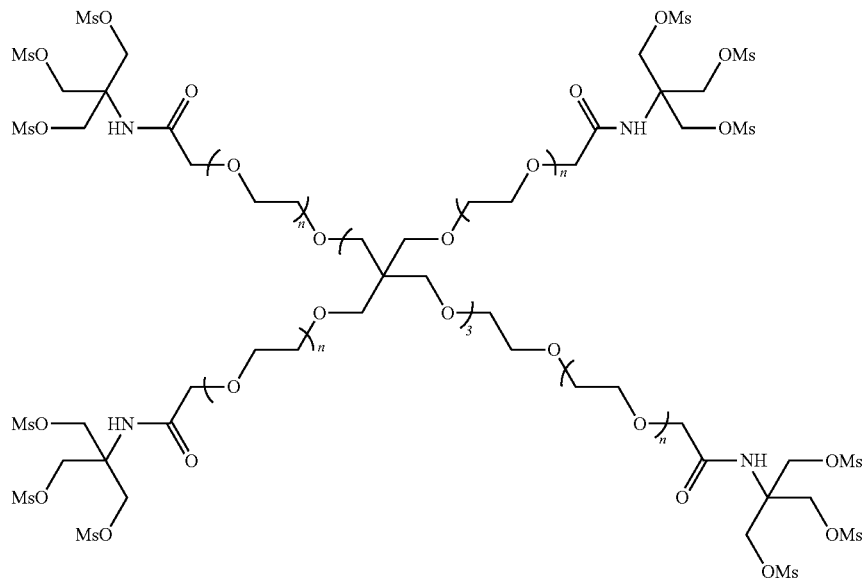

7

A compound 6 (60 g, 3 mmol, prepared in Example 6) and toluene (600 mL) were added to a reaction flask, heated and refluxed; after 120 mL of toluene was distilled off, the heating was stopped; after the remaining was cooled to room temperature, methylene chloride (60 mL) and triethylamine (5.4 mL) were added, stirred evenly, cooled with ice water, and then added dropwise with methanesulfonyl chloride (2.8 mL), and after adding dropwise, a cold bath was removed, and the remaining was naturally raised at a room temperature, and then reacted overnight. Ethanol (6 mL) was added to the reaction system next day, stirred and filtered, and then concentrated, and residues were added with isopropanol, heated for dissolved clarification, and then cooled and crystallized. The remaining was filtered and dried to obtain 59 g of product. $^1$H NMR: (DMSO): 3.16 (s, 72H), 3.53 (m, 1800H), 3.63 (s, 48H), 3.82 (s, 16H), 4.28 (m, 16H), 8.20 (s, 8H).

Example 8 Preparation of N-[2-azido-1,1-bis(azidomethyl)ethyl]-oct-arm polyethylene glycol (20K) Carboxylic Acid Amide

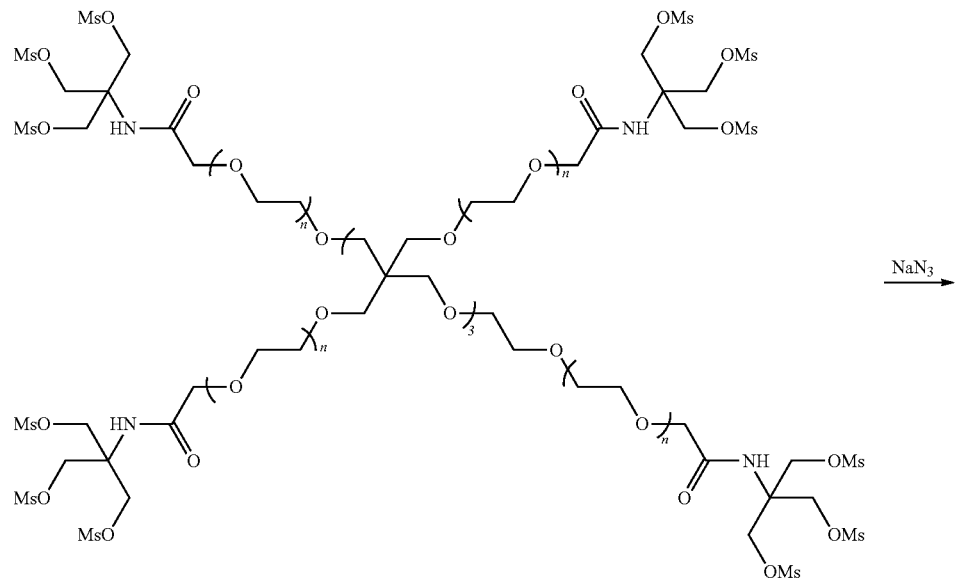

7

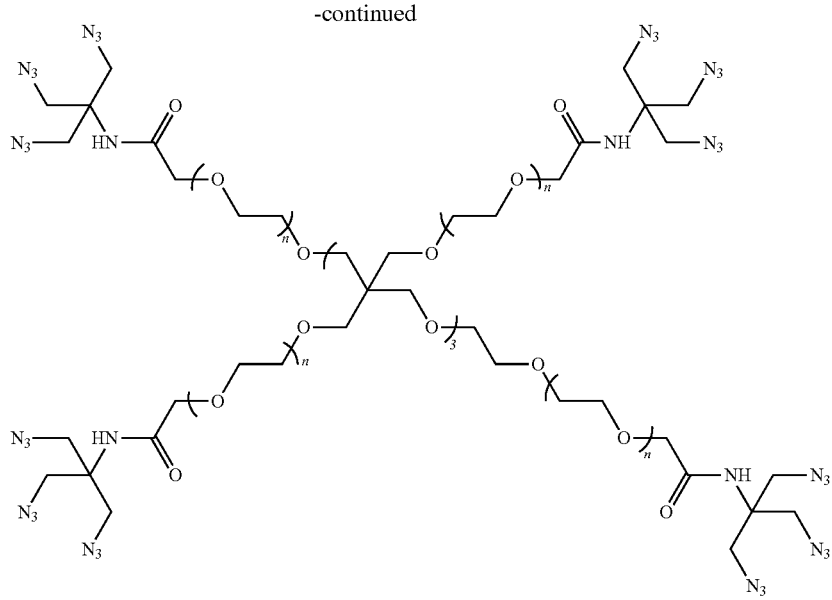

8

A compound 7 (58.9 g, 2.94 mmol, prepared in Example 7) and sodium azide (3.1 g, 47 mmol) were added to a reaction flask, added with N,N-dimethylformamide (295 mL), and heated to 90° C. and reacted for 5 hours, then the heating was stopped, and after the mixture was cooling to room temperature, water (295 mL) and 15% sodium chloride solution were added to a system, stirred for dissolution, extracted with methylene chloride (240 mL+180 mL+120 mL), then organic phases were combined, and the remaining was dried. The remaining was filtered and concentrated, and residues were cooled and then precipitated with diethyl ether, then subjected to suction filtration, and dried to obtain 52 g of product. $^1$H NMR: (DMSO): 3.53 (m, 1800H), 3.61 (s, 48H), 3.82 (s, 16H), 4.28 (m, 16H), 8.20 (s, 8H).

Example 9 Preparation of Tetra-Arm Polyethylene Glycol (10K) Carboxylic Acid Amide Butyl Tri(Propargyl Ether)

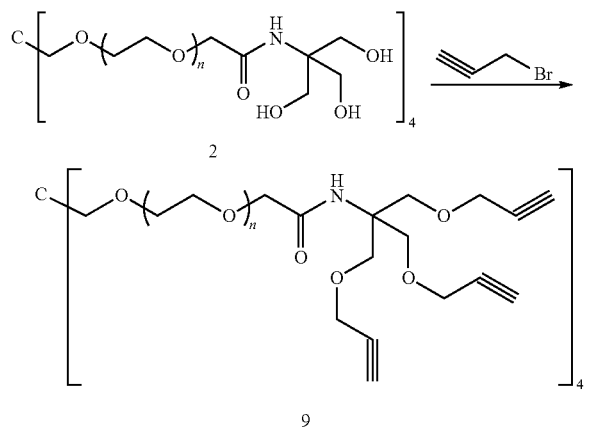

9

A compound 2 (10 g, 0.5 mmol, prepared in Example 2) was dissolved in tetrahydrofuran (150 mL), cooled to 0° C. under nitrogen protection, added with sodium hydride (0.48 g), reacted for half an hour at room temperature, added with 22.4 mL of bromopropyne and 0.09 g of potassium iodide, heated and refluxed in the dark for 2 hours, then cooled and added with 100 mL of water, and concentrated to remove the tetrahydrofuran; residues were extracted with methylene chloride, then the extracted solution was washed, dried, filtered, and concentrated, and a residual solution was precipitated with diethyl ether, filtered and dried in vacuum to obtain 8.4 g of product. $^1$H NMR: (DMSO): 3.34 (s, 12H), 3.53 (m, 900H), 3.66 (s, 8H), 4.19 (s, 24H), 4.37 (s, 8H), 8.20 (s, 4H).

Example 10 Preparation of Tetra-Arm Polyethylene Glycol (10K) Carboxylic Acid Amide Butyl Tri(Tert-Butyl Oxyacetate)

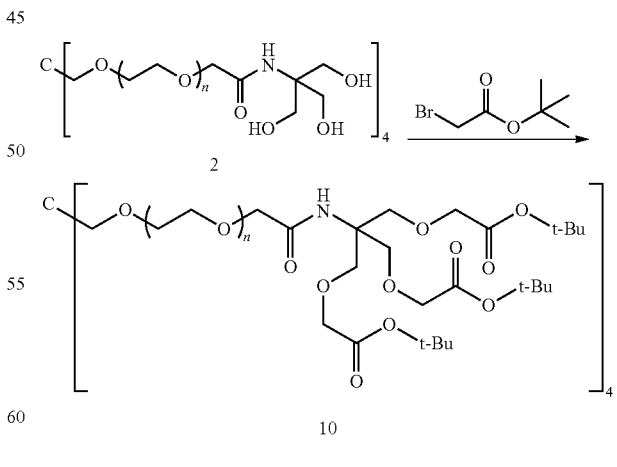

10

A compound 2 (10 g, 0.5 mmol, prepared in Example 2) was dissolved in DMF (30 mL), cooled to 0° C. under nitrogen protection, added with sodium hydride (0.48 g), reacted for half an hour at room temperature, then added with tert-butyl bromoacetate, reacted overnight at room temperature, then cooled and added with 100 mL of water, and extracted with methylene chloride, then the extracted solution was washed, dried, filtered, and concentrated, and a residual solution was precipitated with isopropanol, filtered and dried in vacuum to obtain 8.8 g of product. $^1$H NMR: (DMSO): 1.43 (s, 108H), 3.53 (m, 900H), 3.66 (s, 8H), 4.35 (s, 8H), 4.41 (s, 24H), 8.20 (s, 4H).

Example 11 Preparation of Tetra-Arm Polyethylene Glycol (10K) Carboxylic Acid Amide Butyl Tri(Oxyacetic Acid)

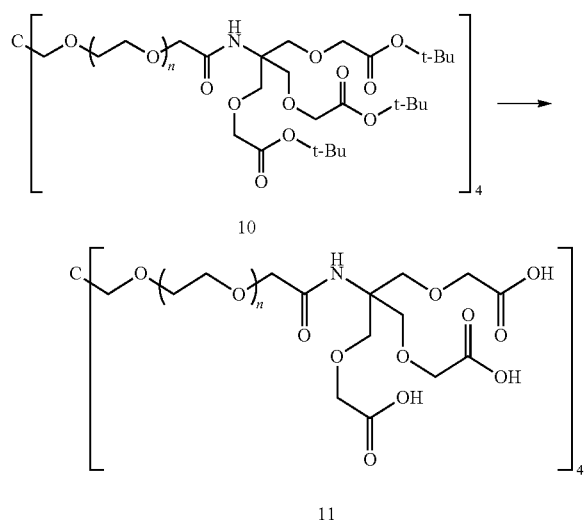

A compound 10 (prepared in Example 10) was dissolved in methanol (100 mL), added with 1.0 M sodium hydroxide solution (100 mL), heated to 60° C. and reacted for 5 hours, and then concentrated to remove the methanol; residues were acidified with diluted hydrochloric acid, and extracted with methylene chloride, then the extracted solution was washed, dried, filtered, and concentrated, and a residual solution was precipitated with isopropanol, filtered and dried in vacuum to obtain 7.6 g of product. $^1$H NMR: (DMSO): 3.09 (s, 12H), 3.53 (m, 900H), 3.66 (s, 8H), 4.25 (s, 24H), 4.33 (m, 32H), 8.20 (s, 12H), 8.23 (s, 4H).

Example 12 Preparation of Tetra-Arm Polyethylene Glycol (10K) Carboxylic Acid Amide Butyl Tri(Oxyacetate Propargylamide)

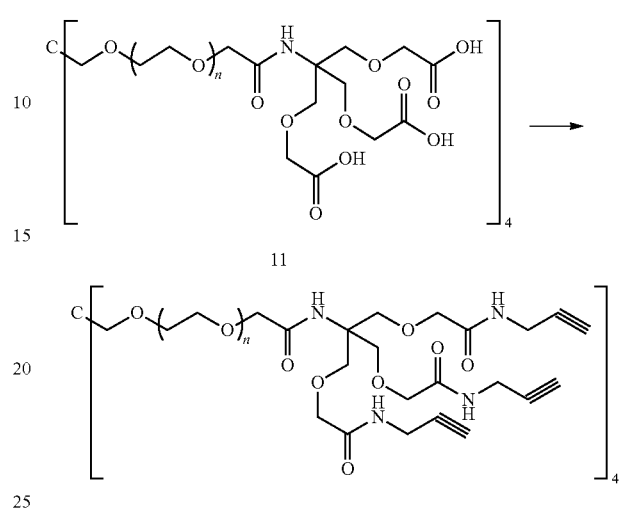

A compound 11 (prepared in Example 11) and N-hydroxysuccinimide (0.6 g) were dissolved in 100 mL of methylene chloride, added with N,N'-dicyclohexylcarbodiimide (1.5 g), reacted for 4 hours, then added with 1 mL of propargylamine, reacted overnight at room temperature, and filtered; then a reaction solution was concentrated, then residues were precipitated with isopropyl alcohol, and subjected to extraction filtration, and an obtained solid was dried in vacuum to obtain 7.2 g of product. $^1$H NMR: (DMSO): 3.09 (s, 12H), 3.53 (m, 900H), 3.66 (s, 8H), 4.25 (s, 24H), 4.33 (m, 32H), 8.20 (s, 12H), 8.23 (s, 4H).

Example 13 Preparation of N-[2-azido-1,1-bis(azidomethyl)ethyl]-tetra-arm polyethylene glycol (10K) Carboxylic Acid Amide and Bupivacaine Conjugate (L1)

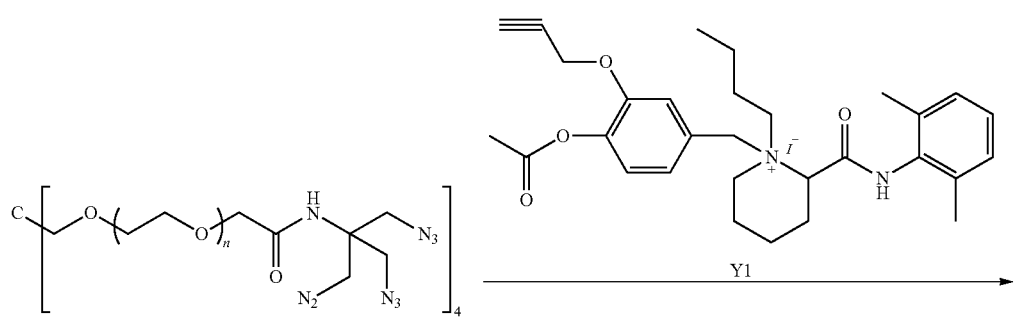

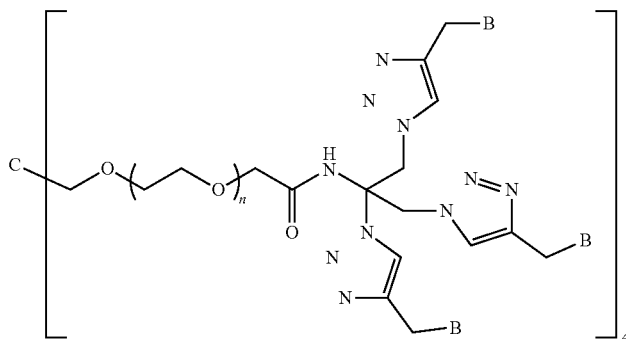

L1

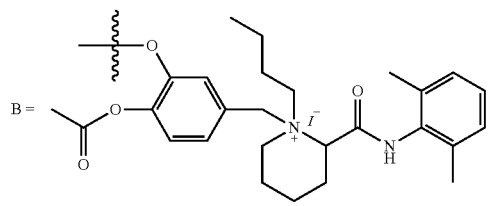

N-[2-azido-1,1-bis(azidomethyl)ethyl]-tetra-arm polyethylene glycol (10K) carboxylic acid amide (10K, 10 g, 1 mmol, prepared in Example 4), a compound Y1 (9.3 g, 15 mmol) and vitamin C (2.2 g, 125 mmol) were added into N,N-dimethylformamide (200 mL), quickly stirred for dissolution, then added with an aqueous solution (44 mL) of copper sulfate pentahydrate (0.38 g, 15 mmol), reacted overnight at room temperature, and precipitated with isopropanol to obtain 8.6 g of product. $^1$H NMR: (DMSO): 0.92 (t, 36H), 1.33 (m, 48H), 1.79 (m, 48H), 2.15 (s, 72H), 2.21 (m, 24H), 2.34 (s, 36H), 2.60 (s, 12H), 3.23 (m, 36H), 3.53 (m, 900H), 3.66 (s, 8H), 3.91 (s, 24H), 4.35 (s, 8H), 4.59 (m, 36H), 6.89 (m, 24H), 7.08 (m, 48H), 7.69 (s, 12H), 8.20 (m, 4H), 9.82 (s, 12H).

Example 14 Determination of Drug Loading Capacities of N-[2-azido-1,1-bis(azidomethyl)ethyl]-tetra-arm polyethylene glycol (10K) Carboxylic Acid Amide and Bupivacaine Conjugate (L1)

About 50 mg of N-[2-azido-1,1-bis(azidomethyl)ethyl]-tetra-arm polyethylene glycol (10K) carboxylic acid amide and bupivacaine conjugate (L1, prepared in Example 13) were weighed accurately, placed in a 30 mL volumetric flask, and added with 10 mL of 0.1 mol/L hydrochloric acid for dissolution, then the mixture was shaken evenly, plugged, capped, placed in a 60° C. constant-temperature drying cabinet for 20 hours, and cooled down, and used as a test solution. Another 25 mg of bupivacaine hydrochloride reference substance was weighed accurately, placed in a 10 mL volumetric flask, dissolved with 0.1 mol/L hydrochloric acid and diluted to a scale, and 5 mL of the mixture was weighed accurately, placed in a 25 mL volumetric flask, diluted with 0.1 mol/L hydrochloric acid to a scale, and used as a reference substance solution. A content of irinotecan in the sample L1 was determined to be 19.7% by high performance liquid chromatography.

Example 15 Preparation of Azioacetic Acid

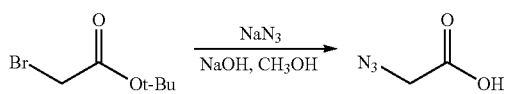

Tert-butyl bromoacetate (5.82 g, 30 mmoL) was added to a reaction flask, and dissolved with acetone (80 mL), then added with a solution formed by dissolving sodium azide (4.55 g, 70 mmoL) in water (40 mL), and heated and refluxed overnight. A reaction solution was distilled to remove the acetone, residues were extracted with diethyl ether, the extracted solution was washed with saturated brine, dried, and concentrated under a reduced pressure to obtain an oily liquid. The liquid was dissolved with methanol (90 mL), then added with a 1N sodium hydroxide solution (90 mL), stirred, and heated and refluxed for 3 hours. After cooling, the methanol was distilled off under a reduced pressure, a residual solution was cooled in an ice bath, and added with 6N hydrochloric acid to regulate a pH value to 2, and then the remaining was extracted with diethyl ether, and the extracted solution was washed with water, dried and concentrated to obtain azioacetic acid, wherein MS m/z: 124 [M+Na]$^+$.

Example 16 Preparation of Irinotecan Azidoacetate (Y2)

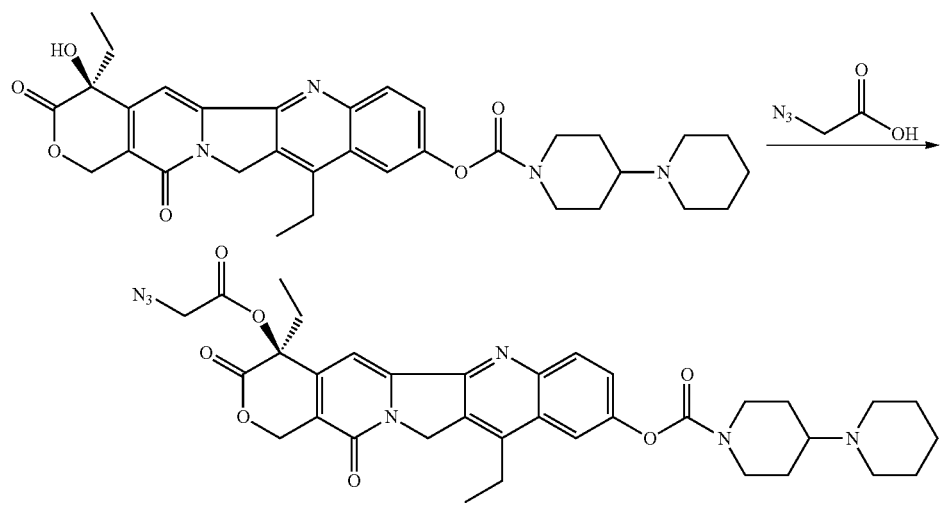

Azioacetic acid (2.5 g, 25 mmoL) and irinotecan (14.7 g, 25 mmoL) were added to a reaction flask, dissolved with methylene chloride, and cooled in an ice bath, and then 4-dimethylaminopyridine (DMAP, 6.1 g, 50 mmol) and 1-(3-dimethylaminopropyl)-3-ethylcarbodiimide hydrochloride (EDCI, 10.3 g, 50 mmol) were added to the reaction flask, and stirred continuously at room temperature overnight after addition. After a reaction solution was concentrated, residues were purified through column chromatography to obtain 14.2 g of irinotecan azidoacetate (Y2), wherein a yield was 57%, and MS m/z: 692 [M+Na]+.

Example 17 Preparation of Tetra-Arm Polyethylene Glycol (10K) Carboxylic Acid Amide Butyl Tri(Propargylamide Oxyacetate) and an Irinotecan Azidoacetate Conjugate (L2)

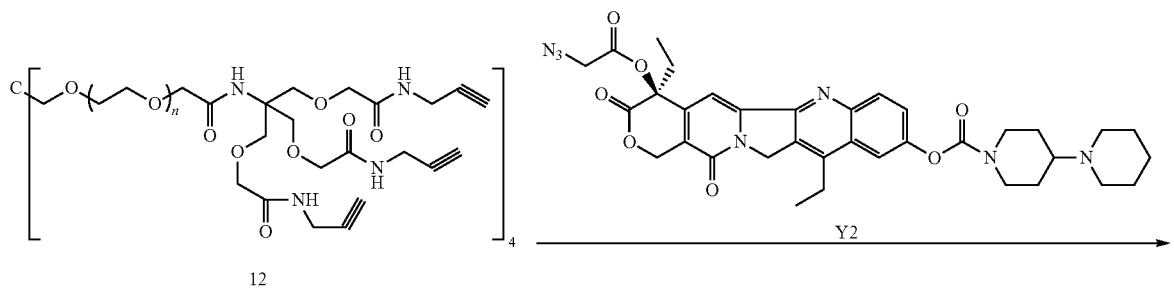

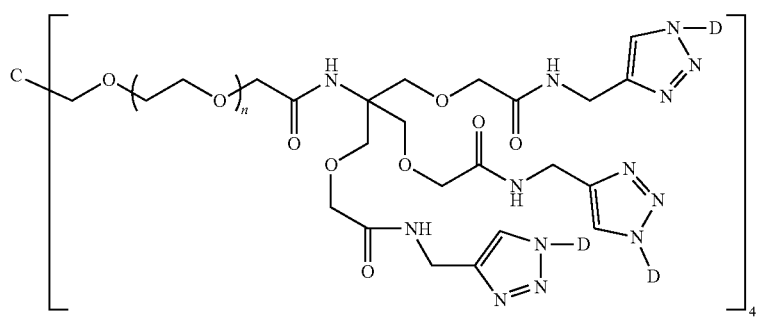

-continued

D = 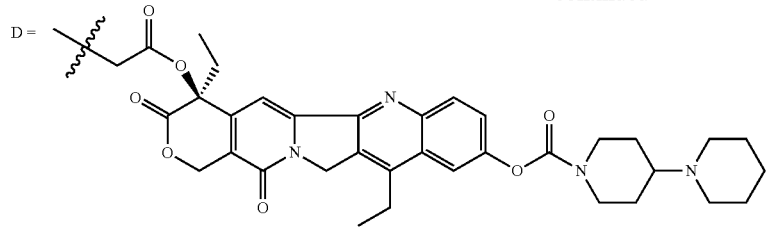

Tetra-arm polyethylene glycol (10K) carboxylic acid amide butyl tri(propargylamide oxyacetate) (10K, 10 g, 1 mmol, prepared in Example 12), a compound Y2 (10.0 g, 15 mmol) and vitamin C (2.2 g, 125 mmol) were added to N,N-dimethylformamide (200 mL), quickly stirred for dissolution, then added with an aqueous solution (44 mL) of copper sulfate pentahydrate (0.38 g, 15 mmol), reacted overnight at room temperature, and precipitated with isopropanol to obtain 8.9 g of product. $^1$H NMR: (DMSO): 0.92 (t, 12H), 1.22 (t, 12H), 1.52 (m, 24H), 1.86 (m, 24H), 2.32 (s, 8H), 2.56 (m, 20H), 3.53 (m, 900H), 3.66 (s, 8H), 4.16 (s, 24H), 4.23 (s, 8H), 4.28 (s, 8H), 4.33 (s, 24H), 4.79 (s, 8H), 6.81 (s, 4H), 7.50 (m, 12H), 8.20 (s, 4H), 8.41 (s, 12H), 8.67 (s, 12H).

Example 18 Determination of Drug Loading Capacities of Tetra-Arm Polyethylene Glycol (10K) Carboxylic Acid Amide Butyl Tri(Propargylamide Oxyacetate) and an Irinotecan Azidoacetate Conjugate (L2)

About 25 mg of tetra-arm polyethylene glycol (10K) carboxylic acid amide butyl tri(propargylamide oxyacetate) and irinotecan irinotecan azidoacetate conjugate (L2, prepared in Example 17) were weighed accurately, placed in a 25 mL volumetric flask, added with 2 mL of water, and then added with 20 mL of 0.005 mol/L sodium hydroxide solution for dissolution, then the mixture was shaken evenly, heated for 30 minutes in a 40° C. water bath, cooled down, diluted to a scale with 0.04 mol/L hydrochloric acid solution, shaken evenly, and used as a test solution. Another 25 mg of irinotecan hydrochloride standard substance was weighed accurately, placed in a 25 mL volumetric flask, dissolved with water and diluted to a scale; 2 mL of the mixture was weighed accurately, placed in a 25 mL volumetric flask, then added with 20 mL of 0.005 mol/L sodium hydroxide solution, heated for 30 minutes with the test solution in a 40° C. water bath, cooled down, diluted to a scale with 0.04 mol/L hydrochloric acid solution, shaken evenly, and used as a standard solution. A content of irinotecan in the sample L2 was determined to be 28.1% by high performance liquid chromatography.

What is claimed is:
1. A polyethylene glycol derivative of general formula I',

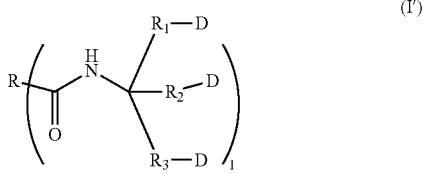

(I')

wherein:
R

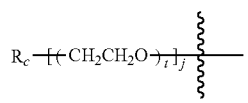

has a structure as follows:

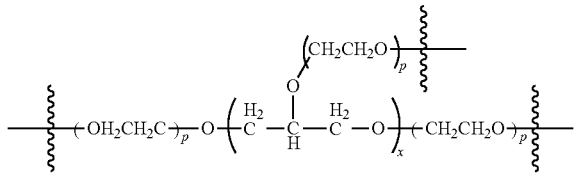

wherein, p is an integer of 3 to 250,
x is an integer of 1 to 18, and
the l is equal to x+2; or,
R has a structure as follows:

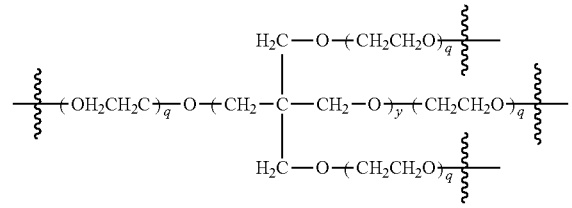

wherein, q is an integer of 3 to 250,
y is an integer of 1 to 9, and
the l is equal to 2y+2;
$R_1$, $R_2$ and $R_3$ are independently selected from one or a combination of more than two of —$(CH_2)_i$—, —$(CH_2)_iO(CH_2)_i$—, —$(CH_2)_iO(CH_2)_i$CONH$(CH_2)_i$—, —$(CH_2)_i$NH—, —$(CH_2)$OCOO—, —$(CH_2)_i$OCONH—, —$(CH_2)_i$NHCO—, —$(CH_2)_i$NHCOO—, —$(CH_2)_i$NHCONH—, —OC$(CH_2)_i$COO—, —$(CH_2)_i$COO— and —$(CH_2)_i$CONH—; and i is an integer of 0 to 10;
D is —$N_3$ or —C≡CH;
l is selected from an integer of 1 to 20.
2. The polyethylene glycol derivative of claim 1, wherein the l is an integer selected from 3 to 8.
3. The polyethylene glycol derivative of claim 1, wherein the polyethylene glycol derivative has a molecular weight of 1000 Da to 80000 Da.
4. The polyethylene glycol derivative of claim 1, wherein the polyethylene glycol derivative has a structure of general formula II or III:

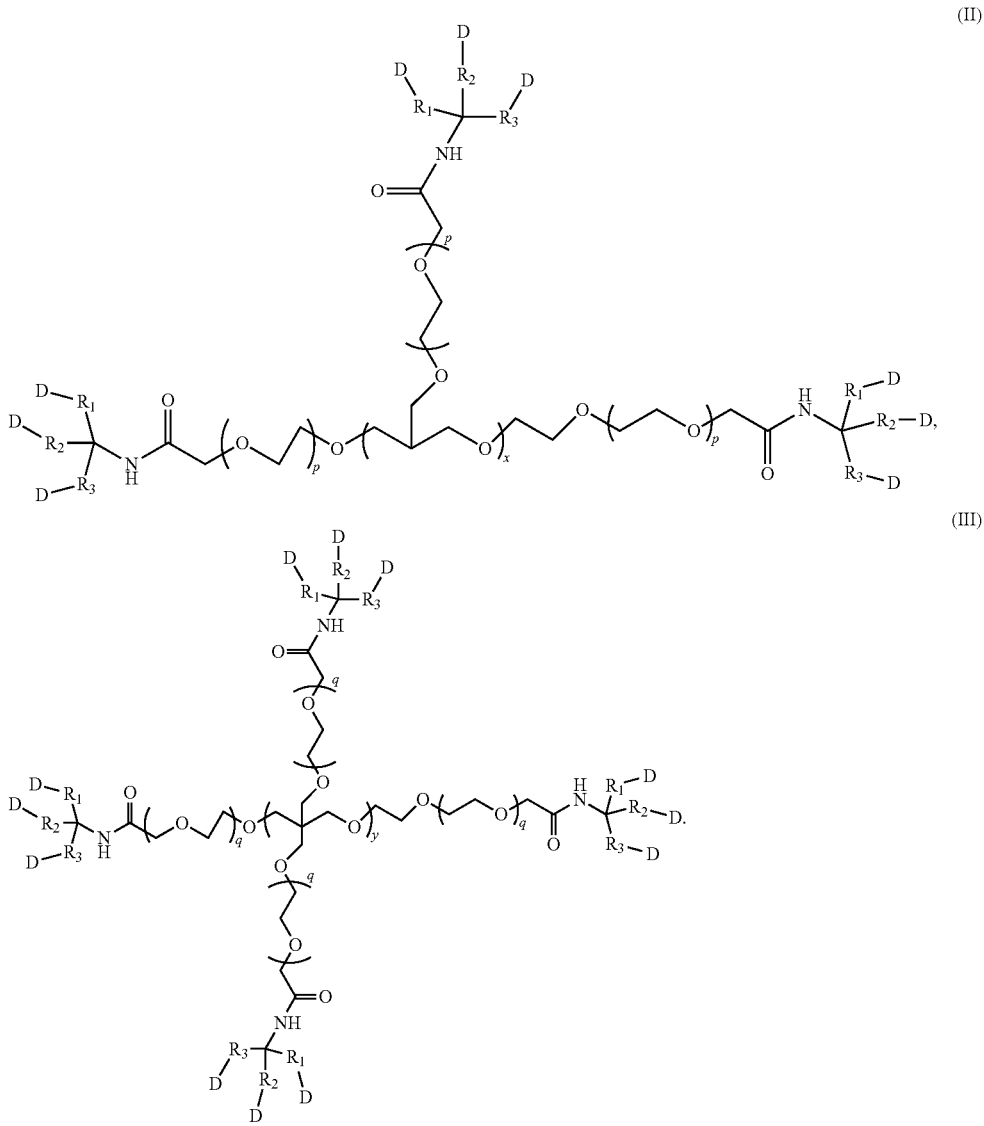

5. The polyethylene glycol derivative of claim 1, wherein the D is —$N_3$, the $R_1$, the $R_2$ and the $R_3$ are —$(CH_2)_i$—, and i is an integer of 1 to 10; or, the D is —C≡CH the $R_1$, the $R_2$ and the $R_3$ are —$(CH_2)_iO(CH_2)_i$— or —$(CH_2)_iO(CH_2)_iCONH(CH_2)_i$—, and i is an integer of 1 to 10.

6. A preparation method of the polyethylene glycol derivative of claim 1, comprising:
(1) reacting polyethylene glycol consisting of the structure of R or a derivative thereof with ethyl chloroformate to obtain polyethylene glycol ethyl carboxylate;
(2) reacting the polyethylene glycol ethyl carboxylate with tris(hydroxymethyl)aminomethane to obtain N-[2-hydroxy-1,1-bis(hydroxymethyl)ethyl]-polyethylene glycol carboxylic acid amide;
(3) reacting the N-[2-hydroxy-1,1-bis(hydroxymethyl)ethyl]-polyethylene glycol carboxylic acid amide with methanesulfonyl chloride to obtain N-[2-methanesulfonyloxy-1,1-bis(methanesulfonyloxymethyl)ethyl]-polyethylene glycol carboxylic acid amide; and
(4) reacting the N-[2-methanesulfonyloxy-1,1-bis(methanesulfonyloxymethyl)ethyl]-polyethylene glycol carboxylic acid amide with sodium azide to obtain an azido-terminated polyethylene glycol derivative,
or,
(1) reacting a polyethylene glycol consisting of the structure of R or a derivative thereof with ethyl chloroformate to obtain polyethylene glycol ethyl carboxylate;
(2) reacting the polyethylene glycol ethyl carboxylate with tris(hydroxymethyl)aminomethane to obtain N-[2-hydroxy-1,1-(hydroxymethyl)ethyl]-polyethylene glycol carboxylic acid amide; and
(3') reacting the N-[2-hydroxy-1,1-(hydroxymethyl)ethyl]-polyethylene glycol carboxylic acid amide with bromoalkyne to obtain an alkynyl-terminated polyethylene glycol derivative,
or
(1) reacting a polyethylene glycol consisting of the structure of R or a derivative thereof with ethyl chloroformate to obtain a polyethylene glycol ethyl carboxylate;
(2) reacting the polyethylene glycol ethyl carboxylate with tris(hydroxymethyl)aminomethane to obtain N-[2-hydroxy-1,1-(hydroxymethyl)ethyl]-polyethylene glycol carboxylic acid amide;

(3″) reacting the N-[2-hydroxy-1,1-(hydroxymethyl)ethyl]-polyethylene glycol carboxylic acid amide with tert-butyl bromoalkyl carboxylic acid to obtain polyethylene glycol carboxylic acid amide butyl tri(tert-butyl oxyacetate); and (4″) hydrolyzing the polyethylene glycol carboxylic acid amide butyl tri(tert-butyl oxyacetate) to obtain polyethylene glycol carboxylic acid amide butyl tri(oxyacetic acid), and then reacting the polyethylene glycol carboxylic acid amide butyl tri(oxyacetic acid) with aminoalkyne to obtain an alkynyl-terminated polyethylene glycol derivative.

7. The preparation method of claim 6, wherein the step (1) comprises: adding the polyethylene glycol consisting of the structure of R or the derivative thereof and potassium carbonate to N,N-dimethylformamide, dropwise adding ethyl chloroformate under stirring, warming up to 80° C. to 100° C., stirring for reaction, cooling a mixture to room temperature after reaction, pouring the mixture into ice water, stirring the mixture evenly, extracting with methylene chloride, then washing, drying, filtering, concentrating and crystallizing; the step (2) comprises: adding the product of the step (1), tris(hydroxymethyl)aminomethane and potassium carbonate to dimethyl sulfoxide, warming up to 30° C. to 50° C., stirring for reaction, cooling the mixture to room temperature after reaction, pouring the mixture into ice water, stirring the mixture evenly, extracting with dichloromethane, then washing, drying, filtering, concentrating and crystallizing; the step (3) comprises: heating and refluxing the product of the step (2) and toluene, cooling to room temperature, adding methylene chloride and triethylamine, stirring the mixture evenly, cooling with ice water, dripping methanesulfonyl chloride for reaction, adding ethanol after the reaction is completed, and then stirring, filtering, concentrating and crystallizing; and the step (4) comprises: heating the product of the step (3), sodium azide and N,N-dimethylformamide to 70° C. to 100° C., reacting for 2 hours to 8 hours, cooling to room temperature, adding water and a sodium chloride solution, stirring for dissolution, extracting with methylene chloride, combining organic phases, drying, filtering and concentrating, and cooling a residue and precipitating with diethyl ether to obtain a product.

8. The preparation method of claim 6, wherein the step (3′) comprises: dissolving the product of the step (2) in tetrahydrofuran, and adding sodium hydride to react at room temperature for half an hour, adding bromoalkyne and potassium iodide, heating for 1 hour to 4 hours, cooling and adding water, concentrating and removing tetrahydrofuran, and extracting a residue with methylene chloride to obtain a final product.

9. The preparation method of claim 6, wherein the step (3″) comprises: dissolving the product of the step (2) in dimethylformamide and adding sodium hydride to react at room temperature for 0.5 hour to 2 hours, then adding tert-butyl bromoalkyl carboxylic acid for reaction, and adding water after reaction to obtain N-(trihydroxymethyl)-tetra-arm polyethylene glycol carboxylic acid amide-tert-butyl trialkyl carboxylate; and the step (4″) comprises: dissolving the product of the step (3″) in methanol, adding a sodium hydroxide solution, heating and hydrolyzing to obtain polyethylene glycol carboxylic acid amide butyl tri(oxyacetic acid), dissolving the polyethylene polyethylene glycol carboxylic acid amide butyl tri(oxyacetic acid) and N-hydroxysuccinimide in methylene chloride, adding N,N′-dicyclohexylcarbodiimide, reacting for 2 hours to 6 hours, and then adding aminoalkyne to react to obtain a final product.

10. A conjugate of the polyethylene glycol derivative of claim 1 and a drug molecule, having a structure of general formula IV′:

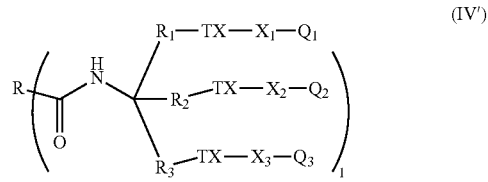

wherein:

R

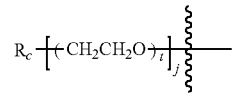

has a structure as follows:

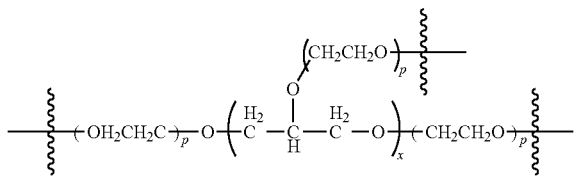

wherein, p is an integer of 3 to 250, x is an integer of 1 to 18, and the l is equal to x+2; or, R has a structure as follows:

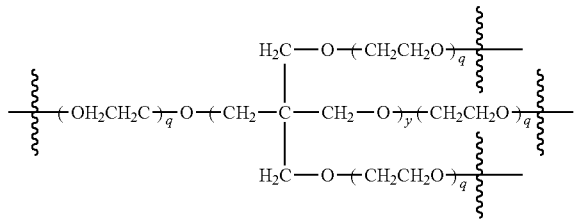

wherein, q is an integer of 3 to 250, y is an integer of 1 to 9, and the l is equal to 2y+2;

$R_1$, $R_2$ and $R_3$ are independently selected from one or a combination of more than two of —$(CH_2)_i$—, —$(CH_2)_iO(CH_2)_i$—, —$(CH_2)_iO(CH_2)_iCONH(CH_2)_i$—, —$(CH_2)_iNH$—, —$(CH_2)_iOCOO$—, —$(CH_2)_iOCONH$—, —$(CH_2)_iNHCO$—, —$(CH_2)_iNHCOO$—, —$(CH_2)_iNHCONH$—, —$OC(CH_2)_iCOO$—, —$(CH_2)_iCOO$— and —$(CH_2)_iCONH$—; and i is an integer of 0 to 10;

l is selected from an integer of 1 to 20;

TX is

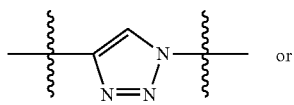

or

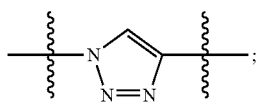

;

$X_1$, $X_2$ and $X_3$ are linking groups independently selected from one or a combination of more than two of —$(CH_2)_a$—, —$(CH_2)_a NH$—, —$(CH_2)_a NHCO$—, —$(CH_2)_a CONH$—, —$(CH_2)_a CO$—, —$(CH_2)_a COO$—, —$(CH_2)_a OCO$—, —$(CH_2)_a SC(O)$—, —$(CH_2)_a O$—, —$(CH_2)_a S$—, $C_3$-$C_{10}$ cycloalkyl, substituted or unsubstituted aryl, and substituted or unsubstituted heterocyclyl, and a is an integer of 0 to 10; and $Q_1$, $Q_2$ and $Q_3$ are drug molecular residues, which are the same or different.

11. The conjugate of claim 10, wherein the conjugate has a structure of general formula V:

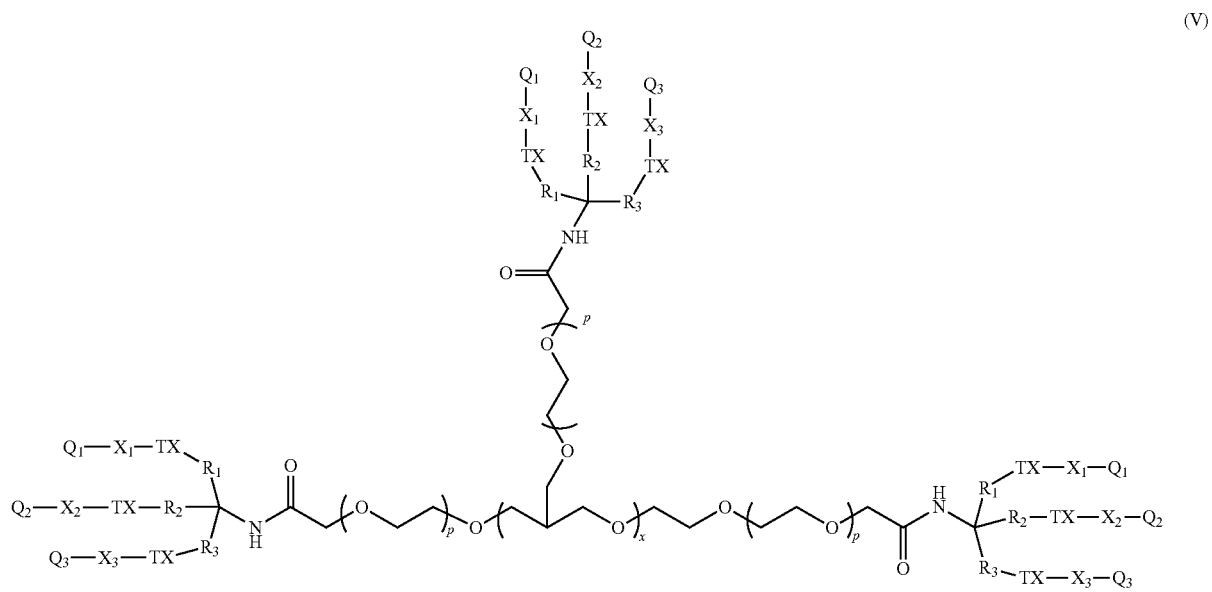

(V)

wherein, p is an integer of 3 to 250, and
x is an integer of 1 to 18; or,
the conjugate has a structure of general formula VI:

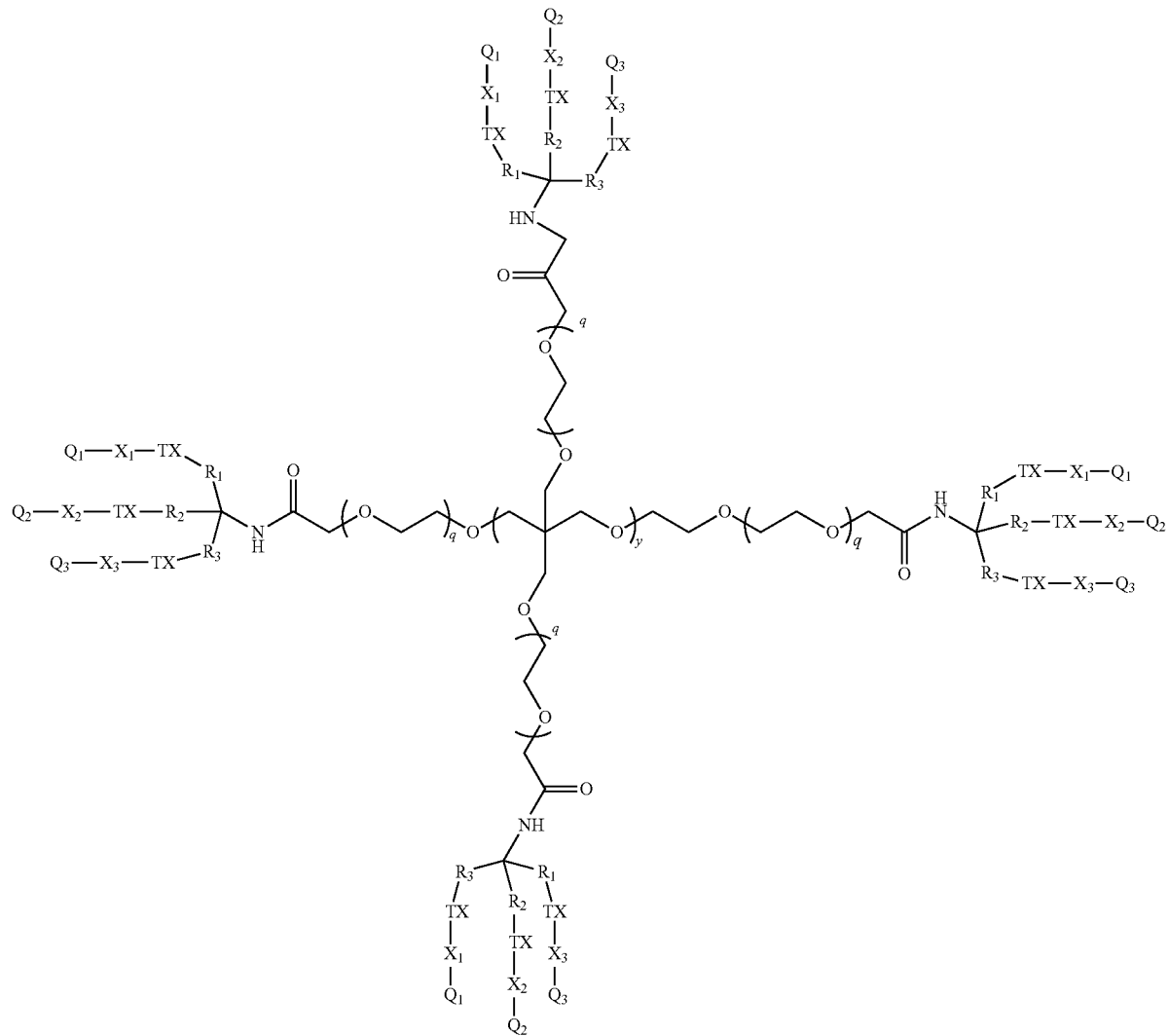

(VI)

wherein, q is an integer of 3 to 250, and
y is an integer of 1 to 19.

12. The conjugate of claim 10, wherein the drug molecule is a local anesthetic.

13. The conjugate of claim 10, wherein the drug molecule is an antineoplastic drug molecule.

14. The conjugate of claim 10, wherein the $Q_1$, the $Q_2$ and the $Q_3$ are the same and are all bupivacaine residues with a following structure of

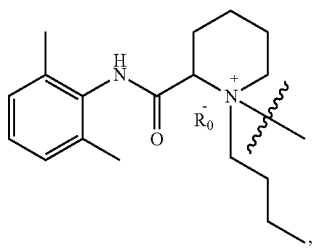

, wherein $R_0^-$ is an anion, such as F–, Cl–, Br–, I–, mesylate, ethylsulfonate, benzene sulfonate, citrate, lactate, succinate, fumarate, glutamate, citrate, salicylate and maleate; or, the $Q_1$, the $Q_2$ and the $Q_3$ are the same and are all irinotecan residues, and specifically, the $Q_1$, the $Q_2$ and the $Q_3$ have a structure as follows:

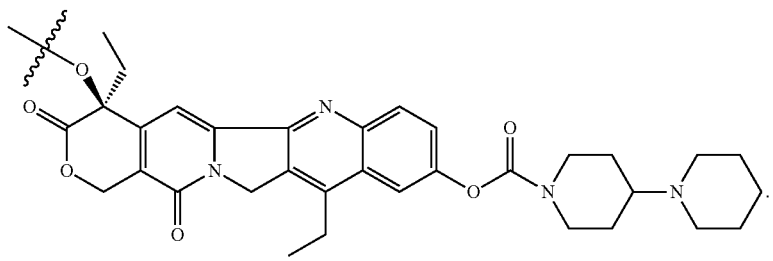 [SMILES: *O[C@]1(CC)C(=O)OCc2c1cc1n(c2=O)Cc2c-1nc1ccc(OC(=O)N3CCC(N4CCCCC4)CC3)cc1c2CC]

15. The conjugate of claim 14, wherein the conjugate has a structure as follows:

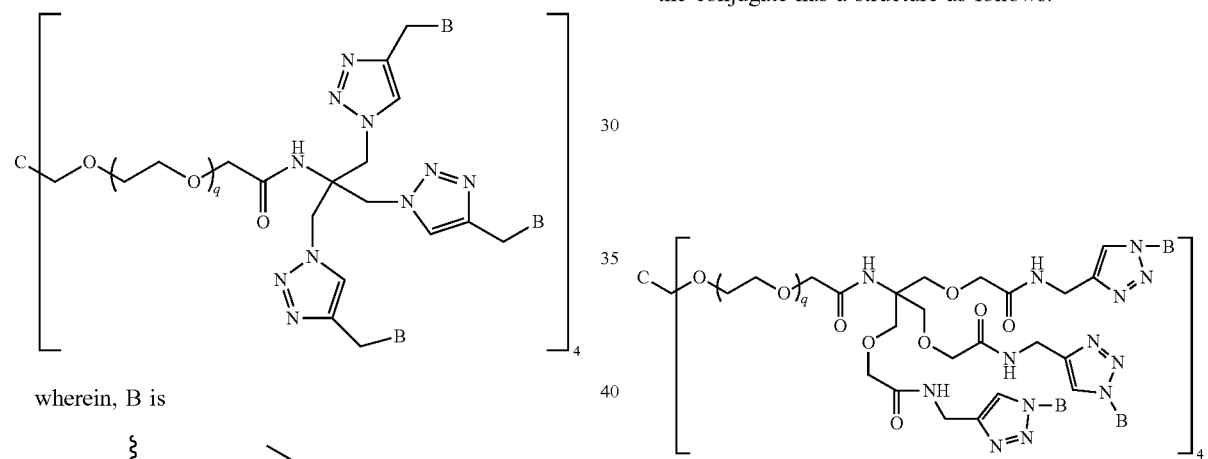

wherein, B is

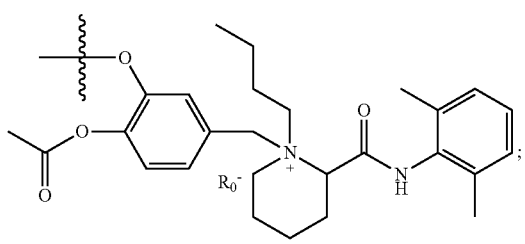

or, the conjugate has a structure as follows:

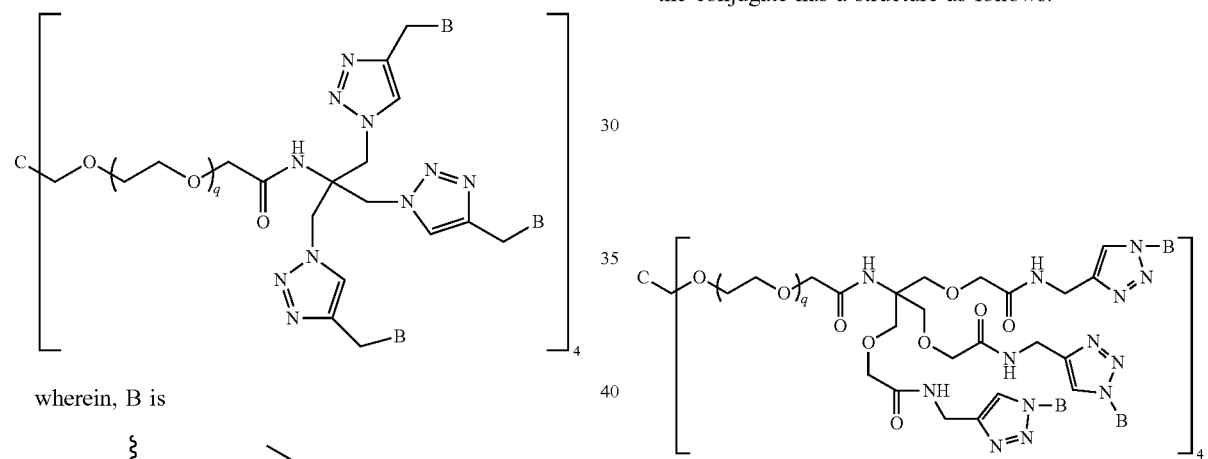

wherein, B is

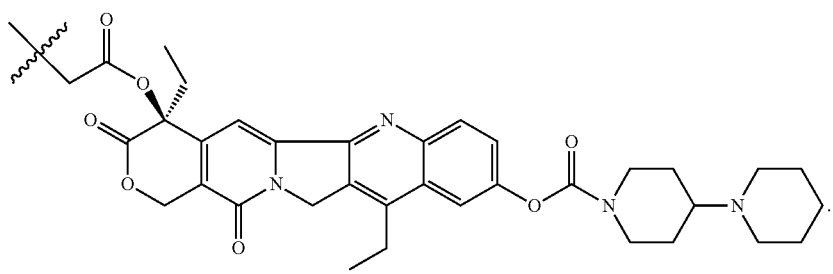 [SMILES: *CC(=O)O[C@]1(CC)C(=O)OCc2c1cc1n(c2=O)Cc2c-1nc1ccc(OC(=O)N3CCC(N4CCCCC4)CC3)cc1c2CC]

16. A pharmaceutical composition comprising the conjugate of claim 10 and a pharmaceutically acceptable carrier or an excipient.

\* \* \* \* \*